(12) United States Patent
Oh et al.

(10) Patent No.: US 9,240,559 B2
(45) Date of Patent: Jan. 19, 2016

(54) PHOSPHORESCENT COMPOUND AND ORGANIC ELECTROLUMINESCENT DEVICE USING THE SAME

(71) Applicant: LG DISPLAY CO., LTD., Seoul (KR)

(72) Inventors: Hyoung-Yun Oh, Gyeonggi-do (KR); In-Bum Song, Seoul (KR); Sung-Hee Park, Gyeonggi-do (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 14/698,531

(22) Filed: Apr. 28, 2015

(65) Prior Publication Data

US 2015/0236275 A1 Aug. 20, 2015

Related U.S. Application Data

(62) Division of application No. 13/283,774, filed on Oct. 28, 2011, now Pat. No. 9,045,471.

(30) Foreign Application Priority Data

Oct. 28, 2010 (KR) .................. 10-2010-0106234
Oct. 29, 2010 (KR) .................. 10-2010-0107314
Oct. 29, 2010 (KR) .................. 10-2010-0107315
Oct. 29, 2010 (KR) .................. 10-2010-0107316

(51) Int. Cl.
| | |
|---|---|
| *H01L 51/54* | (2006.01) |
| *C07D 471/04* | (2006.01) |
| *C09K 11/06* | (2006.01) |
| *H01L 51/00* | (2006.01) |
| *H01L 51/52* | (2006.01) |
| *H01L 51/50* | (2006.01) |

(52) U.S. Cl.
CPC .......... *H01L 51/0072* (2013.01); *C07D 471/04* (2013.01); *C09K 11/06* (2013.01); *C09K 2211/1018* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01)

(58) Field of Classification Search
None
See application file for complete search history.

(56) References Cited

U.S. PATENT DOCUMENTS

2004/0086745 A1* 5/2004 Iwakuma et al. .... C07D 401/10
428/690
2009/0045726 A1 2/2009 Miki et al.

FOREIGN PATENT DOCUMENTS

| EP | 1 961 741 A1 | 8/2008 |
| JP | 2006-080271 A1 | 3/2006 |
| KR | 10-2008-0083276 A | 9/2008 |
| WO | 2006/043440 A1 | 4/2006 |

OTHER PUBLICATIONS

German Office Action dated Sep. 25, 2012 for corresponding German Patent Application No. 10 2011 054 855.6.

* cited by examiner

*Primary Examiner* — Marie R. Yamnitzky
(74) *Attorney, Agent, or Firm* — Morgan, Lewis & Bockius LLP

(57) ABSTRACT

A phosphorescent compound is represented by following Formula:

[Formula]

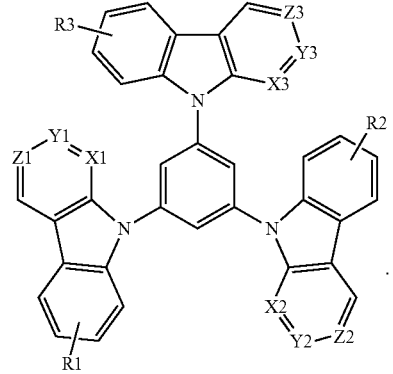

10 Claims, 9 Drawing Sheets

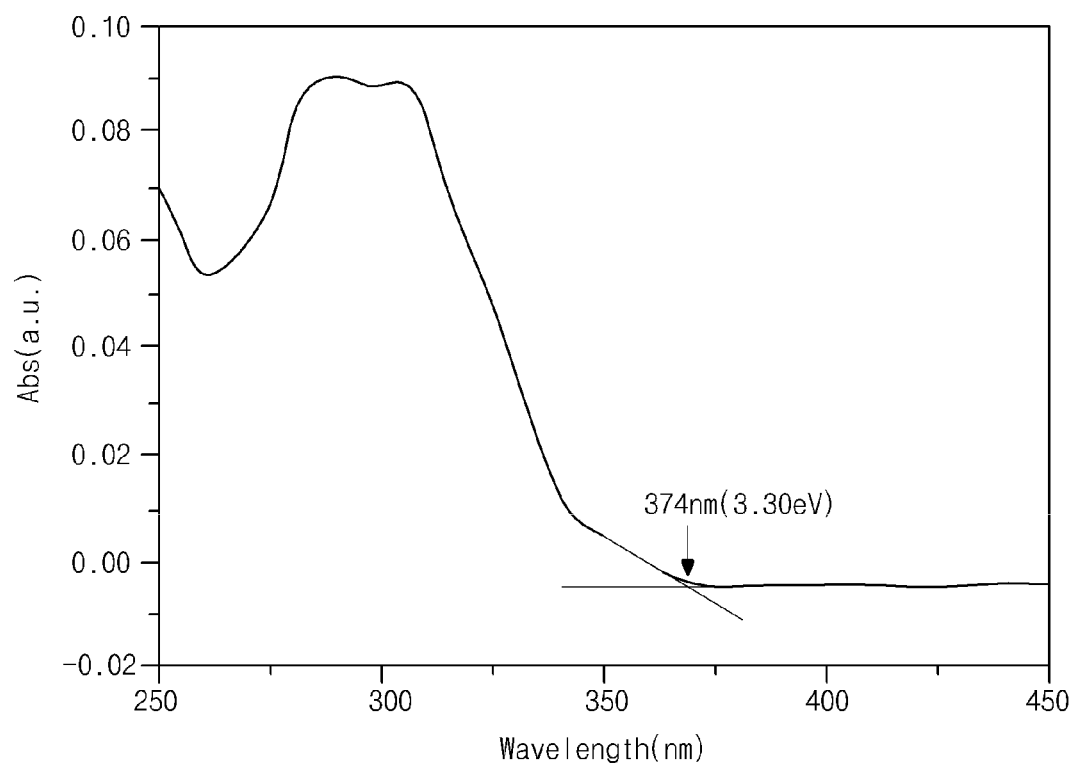

PHOSPHORESCENT COMPOUND AND ORGANIC ELECTROLUMINESCENT DEVICE USING THE SAME

The present application claims the benefit of Korean Patent Application No. 10-2010-0106234 filed in Korea on Oct. 28, 2010, and Korean Patent Application Nos. 10-2010-0107314, 10-2010-0107315, and 10-2010-0107316, filed in Korea on Oct. 29, 2010, respectively, all of which are herein incorporated by reference.

BACKGROUND OF THE INVENTION

1. Field of the Invention

The present invention relates to a phosphorescent compound and an organic electroluminescent device (OELD) and more particularly to a phosphorescent compound having high triplet energy and an OELD using the same.

2. Discussion of the Related Art

An OELD emits light by injecting electrons from a cathode as an electron injection electrode and holes from an anode as a hole injection electrode into an emission compound layer, combining the electrons with the holes, generating an exciton, and transforming the exciton from an excited state to a ground state. A flexible substrate, for example, a plastic substrate, can be used as a base substrate where elements are formed. Since the OELD does not require a backlight assembly, the OELD has low weight and low power consumption. Moreover, the OELD can be operated at a voltage (e.g., 10V or below) lower than a voltage required to operate other display devices.

Dopant is added into a host of the emission layer. For example, a red emission layer includes a host of 4,4'-N,N'-dicarbazolbiphenyl (CBP) of about 30 nm and a dopant of bis(2-phenylquinoline)(aceteylacetonate)iridium(III) (Ir(phq)2acac). The dopant is added by a weight % of about 5 to 10.

Recently, a phosphorescent compound is more widely used for the emission layer than a fluorescent compound. The fluorescent compound only uses singlet energy corresponding to about 25% of excitons for emitting light, and triplet energy corresponding to about 75% of excitons is lost as a heat. However, the phosphorescent compound uses not only the singlet energy but also the triplet energy for emitting light. The phosphorescent dopant includes a heavy atom, such as iridium (Ir), platinum (Pt) and europium (Eu) at a center of an organic compound and has a high electron transition probability from the triplet state to the single state.

However, since an emitting yield of the dopant is rapidly reduced because of a concentration quenching, the dopant cannot comprise the emission layer for itself. Accordingly, a host with the dopant is used for the emission layer.

In the OELD, a hole from the anode and an electron from the cathode are combined in the host of the emission layer such that a singlet state exciton and a triplet state exciton are generated. The singlet state exciton is transited into a singlet energy or a triplet energy of the dopant. The triplet state exciton is transited into a triplet energy of the dopant. Since the exciton transited into the singlet energy of the dopant is re-transited into the triplet energy of the dopant, a destination of all exciton is a triplet energy level of the dopant. The exciton at the triplet energy level of the dopant is transited into a ground state to emit light.

For an efficient energy transition into the dopant, a triplet energy of the host should be larger than that of the dopant. However, referring to FIG. 1, CBP, which is widely used for the host, has a triplet energy of about 2.6 eV, while a phosphorescent dopant, for example, iridium-bis-(4,6-difluorophenylpyridinato-N-C2)-picolinate (FIrpic), has a triplet energy larger than 2.6 eV. Accordingly, an energy counter-transition from the dopant to the host is generated such that an emission yield is reduced. Particularly, the emission yield reduction is strongly generated in a low temperature. To prevent these problems, a new phosphorescent compound having a triplet energy above 2.6 eV and having a thermal stability is required.

In addition, when a triplet energy of the hole transporting layer and the electron transporting layer, which are adjacent to the emission layer, is smaller than that of the dopant, an energy counter-transition from the host or dopant to the hole transporting layer and the electron transporting layer is generated such that an emission yield is also reduced. Accordingly, a triplet energy is an important fact in the hole and electron transporting layers as well as the host.

SUMMARY OF THE INVENTION

Accordingly, the present invention is directed to a phosphorescent compound and an organic electroluminescent device (OELD) using the same that substantially obviates one or more of the problems due to limitations and disadvantages of the related art.

An object of the present invention is to provide a phosphorescent compound having high triplet energy.

Another object of the present invention is to provide an OELD having improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, a phosphorescent compound is represented by following Formula:

[Formula]

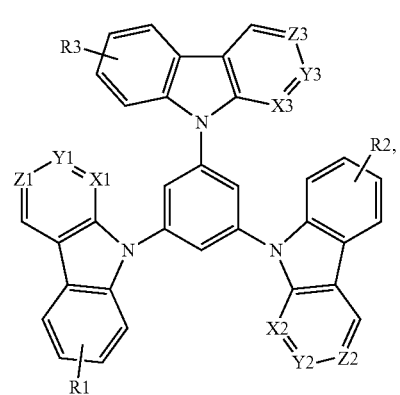

wherein each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen, and wherein each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect of the present invention, a phosphorescent compound is represented by following Formula:

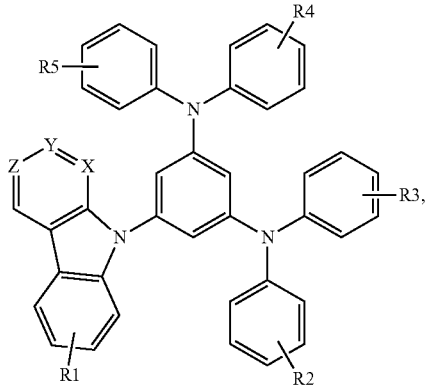

[Formula]

wherein each of X, Y, Z is one of carbon and nitrogen, and at least one of X, Y, Z is nitrogen, and wherein each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, organic electroluminescent device includes a first electrode; a second electrode facing the first electrode; and an emitting material layer between the first and second electrodes, wherein the emitting material layer includes a host represented by following Formula and a dopant,

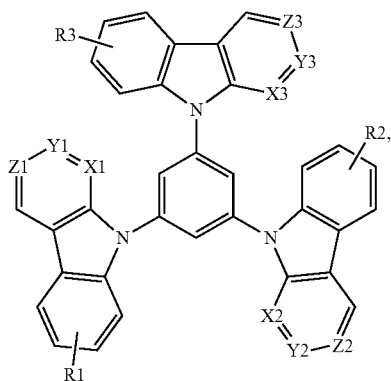

[Formula]

wherein each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen, and wherein each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

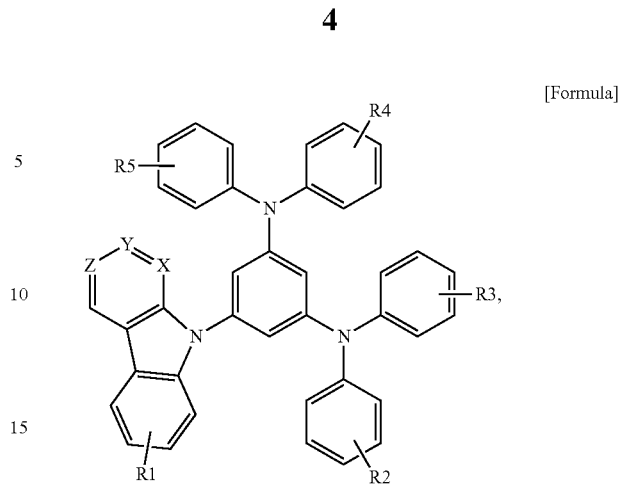

[Formula]

wherein each of X, Y, Z is one of carbon and nitrogen, and at least one of X, Y, Z is nitrogen, and wherein each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

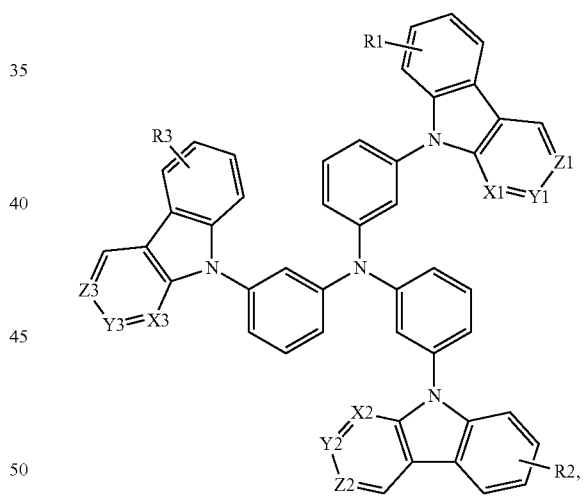

[Formula]

wherein each of X1, X2, X3, Y1, Y2, Y3, Z1, Z2 and Z3 is one of carbon and nitrogen, and each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

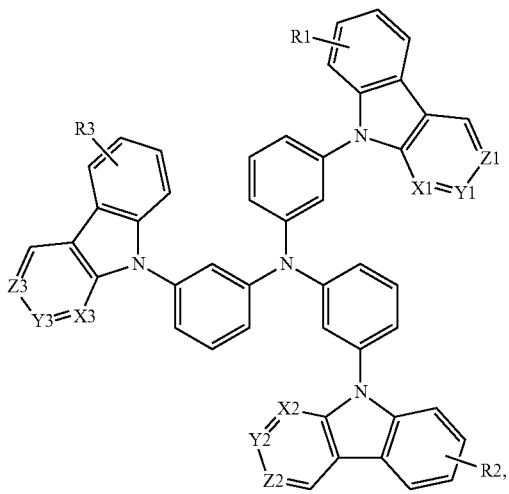

wherein each of X1, X2, X3, Y1, Y2, Y3, Z1, Z2 and Z3 is one of carbon and nitrogen, and each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

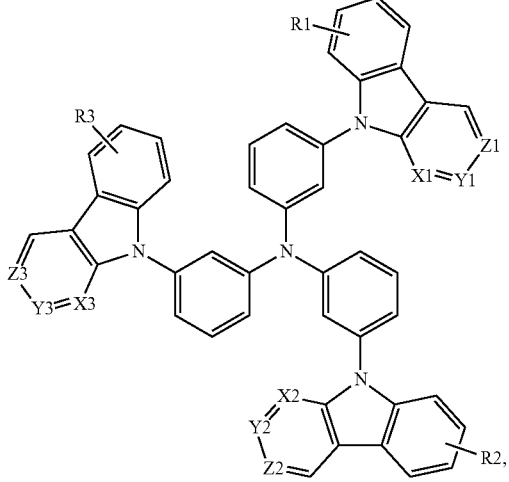

wherein each of X1, X2, X3, Y1, Y2, Y3, Z1, Z2 and Z3 is one of carbon and nitrogen, and each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

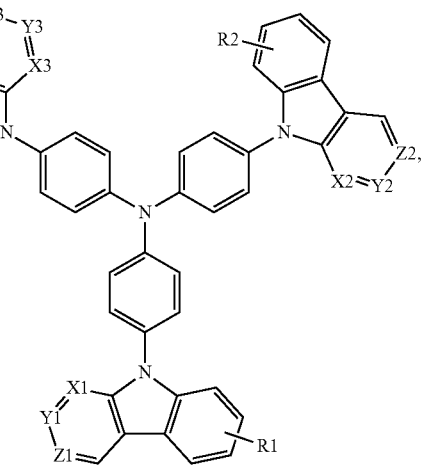

wherein each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen, and wherein each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

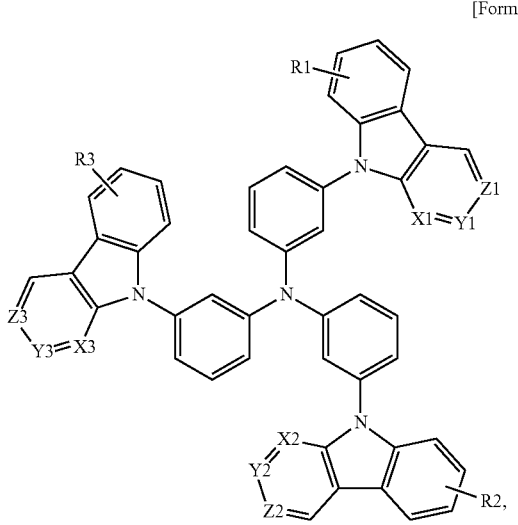

wherein each of X1, X2, Y1, Y2, Z1 and Z2 is one of carbon and nitrogen, and at least one of X1, X2, Y1, Y2, Z1 and Z2 is nitrogen, and wherein each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

[Formula]

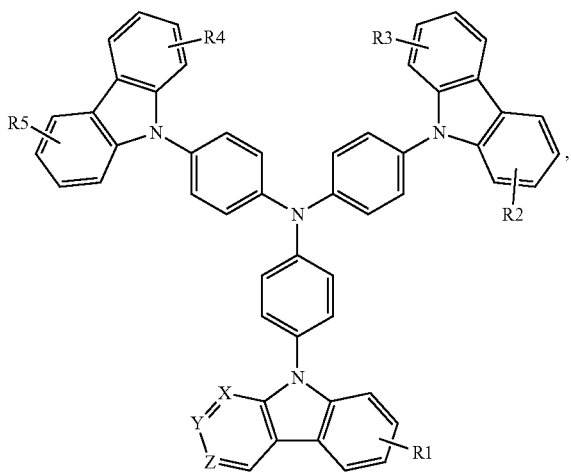

wherein each of X, Y and Z is one of carbon and nitrogen, and at least one of X, Y and Z is nitrogen, and wherein each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

[Formula]

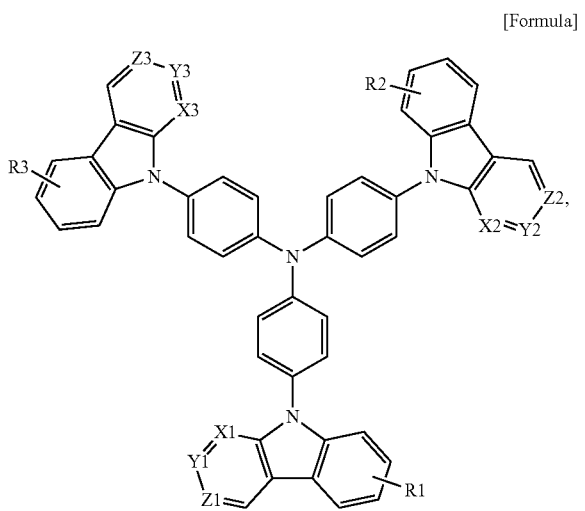

wherein each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen, and wherein each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

[Formula]

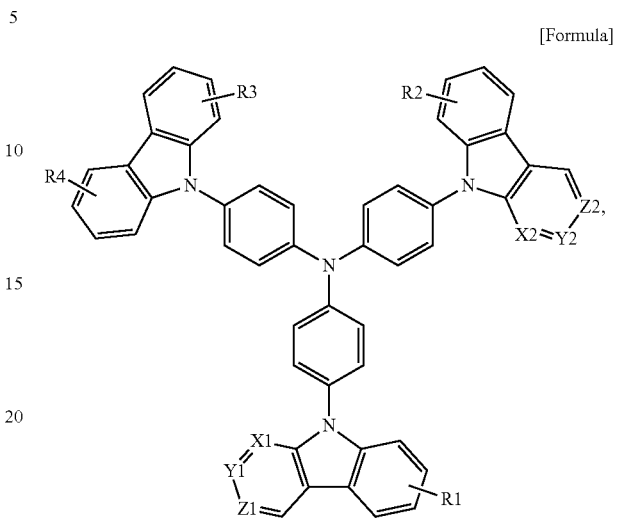

wherein each of X1, X2, Y1, Y2, Z1 and Z2 is one of carbon and nitrogen, and at least one of X1, X2, Y1, Y2, Z1 and Z2 is nitrogen, and wherein each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

[Formula]

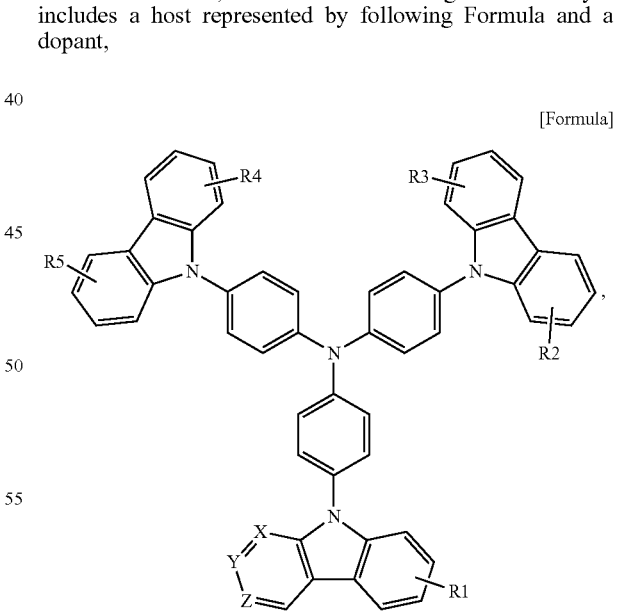

wherein each of X, Y and Z is one of carbon and nitrogen, and at least one of X, Y and Z is nitrogen, and wherein each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

[Formula]

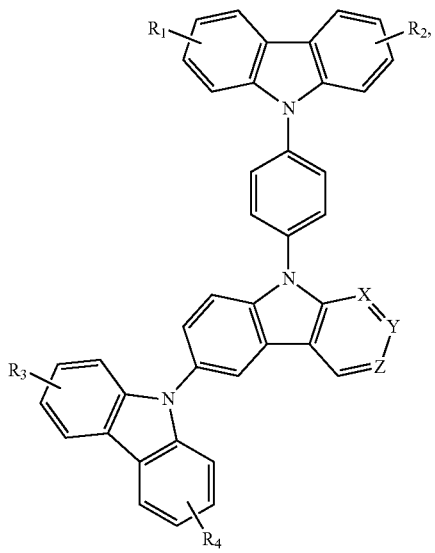

wherein each of X, Y, Z is one of carbon and nitrogen, and at least one of X, Y, Z is nitrogen, and wherein each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, a phosphorescent compound is represented by following Formula:

[Formula]

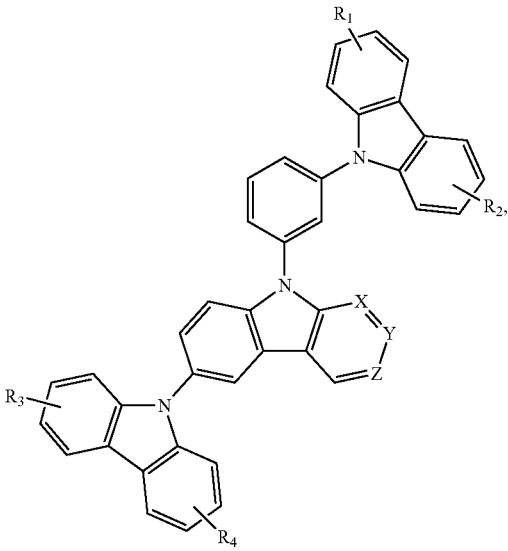

wherein each of X, Y, Z is one of carbon and nitrogen, and at least one of X, Y, Z is nitrogen, and wherein each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

[Formula]

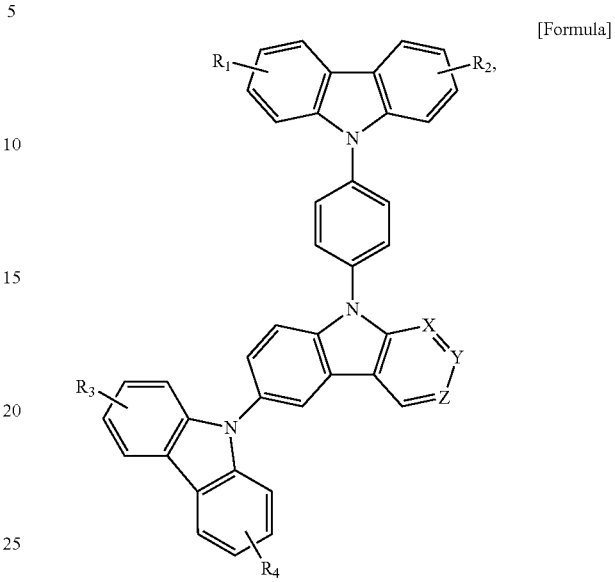

wherein each of X, Y, Z is one of carbon and nitrogen, and at least one of X, Y, Z is nitrogen, and wherein each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group.

In another aspect, an organic electroluminescent device includes a first electrode; a second electrode facing the first electrode; and an emitting material layer between the first and second electrodes, wherein the emitting material layer includes a host represented by following Formula and a dopant,

[Formula]

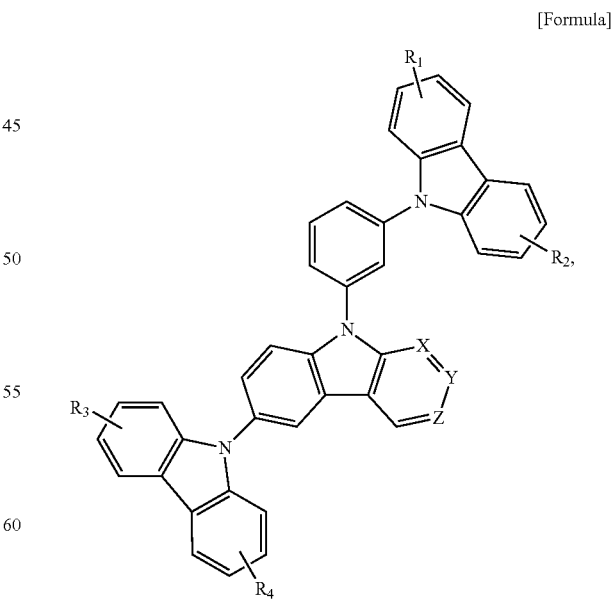

wherein each of X, Y, Z is one of carbon and nitrogen, and at least one of X, Y, Z is nitrogen, and wherein each of R1, R2, R3 and R4 is one of hydrogen (H), fluorine (F), chlorine (Cl), aliphatic group, aromatic group, alkyl silyl group, alkoxy group, aryloxy group, alkyl phosphoryl group, alkyl sulfuryl group, aryl sulfuryl group, alkyl amino group and aryl amino group.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIGS. 3A and 3B show a UV spectrum and a PL spectrum of a phosphorescent compound according to the second embodiment of the present invention.

DETAILED DESCRIPTION OF THE PREFERRED EMBODIMENTS

Figure 1:
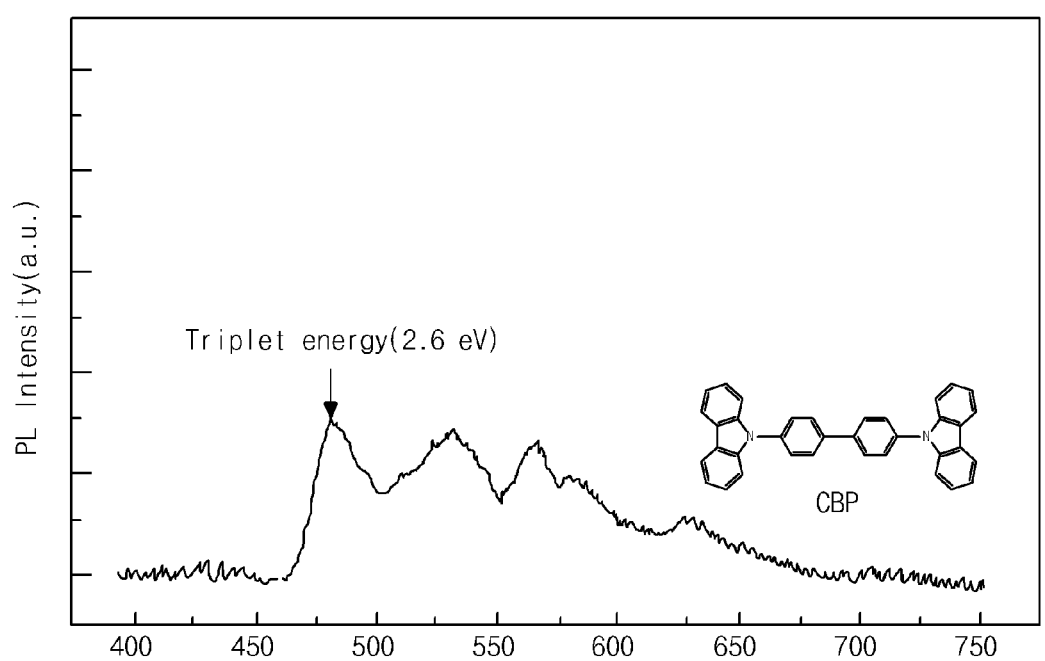
FIG. 1 is a graph showing a photoluminescence (PL) spectrum of CBP as a host for the related art OELD.

Reference will now be made in detail to the preferred embodiments, examples of which are illustrated in the accompanying drawings.

—First Embodiment—

A phosphorescent compound according to the first embodiment of the present invention includes carboline and/or carbozole at 1, 3, and 5 positions of benzene ring. Particularly, carboline substitutes at least one of the 1, 3 and 5 position of the benzene ring. The phosphorescent compound is represented by following Formula 1.

[Formula 1]

In the above Formula 1, each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen. For example, when X1 is nitrogen and both of Y1 and Z1 are carbon, carboline is referred to as α-carboline. When Y1 is nitrogen and both of X1 and Z1 are carbon, carboline is referred to as β-carboline. When Z1 is nitrogen and both of X1 and Y1 are carbon, carboline is referred to as γ-carboline.

In addition, in the above Formula 1, each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formula 1 is one of compounds in following Formula 2.

[Formula 2]

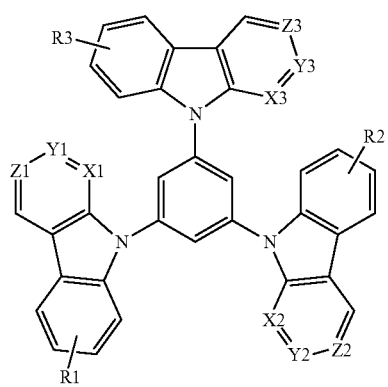

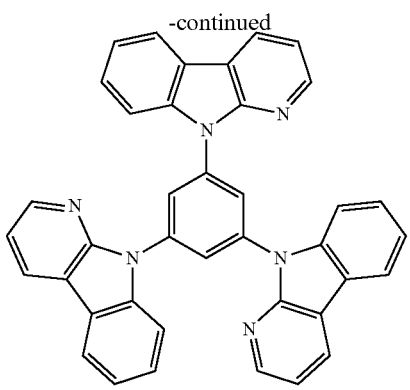

The phosphorescent compound represented by

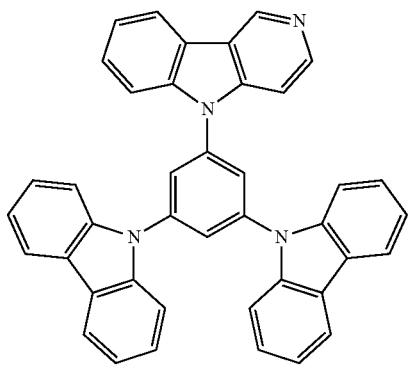 [SMILES: c1ccc2c(c1)c1ccccc1n2-c1cc(-n2c3ccccc3c3ccccc32)cc(-n2c3ccccc3c3cnccc32)c1]

in the above Formula 2 is synthesized by following synthesis.

1. Synthesis of N-(3,5-dibromophenyl)-γ-carboline

N-(3,5-dibromophenyl)-γ-carboline is synthesized by following Reaction Formula 1.

[Reaction Formula 1]

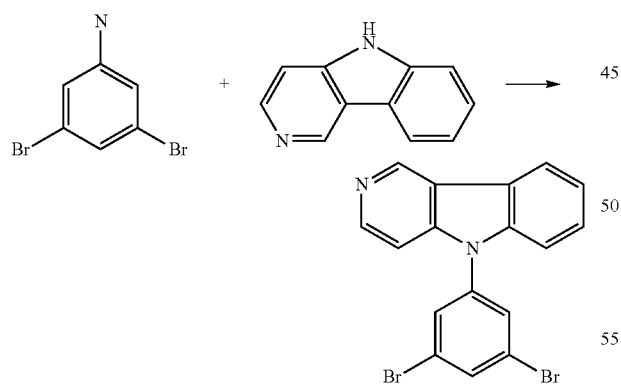

1,3-dibromo-5iodobenzene 5 g (13.8 mmol), γ-carboline 2.33 g (13.8 mmol), dioxane 50 ml, CuI 0.2 g, trans-diaminocyclohexene 0.7 ml and K3PO4 6 g are put in a 100 ml two-neck flask and refluxed for 12 hours. After completion of the reaction, the reaction mixture is filtered to remove a salt and water 50 ml are added in the solution to precipitate. The resulting solution is filtered by column chromatography with ethylene acetate such that white powder 3.0 g is obtained. (yield: 54%)

2. Synthesis of the Phosphorescent Compound

The phosphorescent compound is synthesized by following Reaction Formula 2.

[Reaction Formula 2]

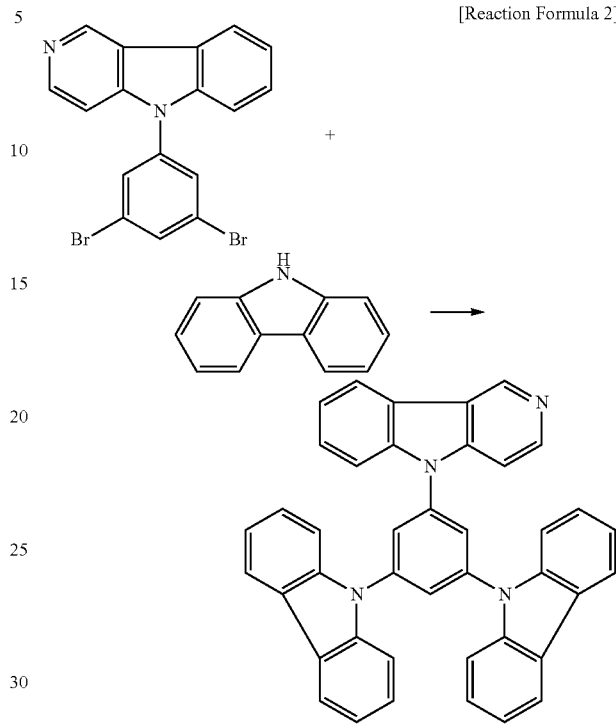

N-(3,5-dibromophenyl)-γ-carboline 2 g (5 mmol), carbazole 1.87 g (11 mmol), toluene 50 ml, Pd2dba3 0.1 g, xantphos 0.23 g and sodium-tert-butoxide 1.3 g are put in a 100 ml two-neck flask and refluxed for 12 hours. After completion of the reaction, the solvent is removed, and the resulting residence is washed with water 50 ml. The resulting solution is filtered by colum chromatography with acetone and hexane of 1:1 such that white powder 0.95 g is obtained. (yield: 70%)

—Second Embodiment—

A phosphorescent compound according to the second embodiment of the present invention includes one carboline and two diphenylamine groups at 1, 3, and 5 positions of benzene ring, respectively. The phosphorescent compound is represented by following Formula 3.

[Formula 3]

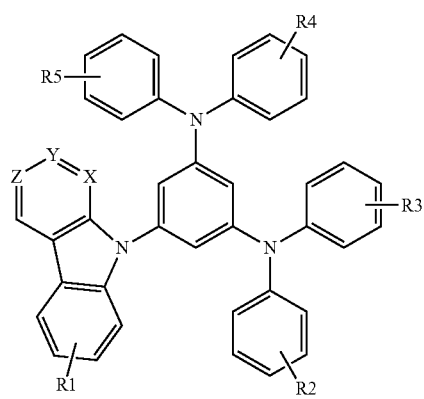

In the above Formula 3, each of X, Y, Z is one of carbon and nitrogen, and at least one of X, Y, Z is nitrogen. For example, when X is nitrogen and both of Y and Z are carbon, carboline is referred to as α-carboline. When Y is nitrogen and both of X and Z are carbon, carboline is referred to as β-carboline. When Z is nitrogen and both of X and Y are carbon, carboline is referred to as γ-carboline.

In addition, in the above Formula 3, each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formula 3 is one of compounds in following Formula 4.

[Formula 4]

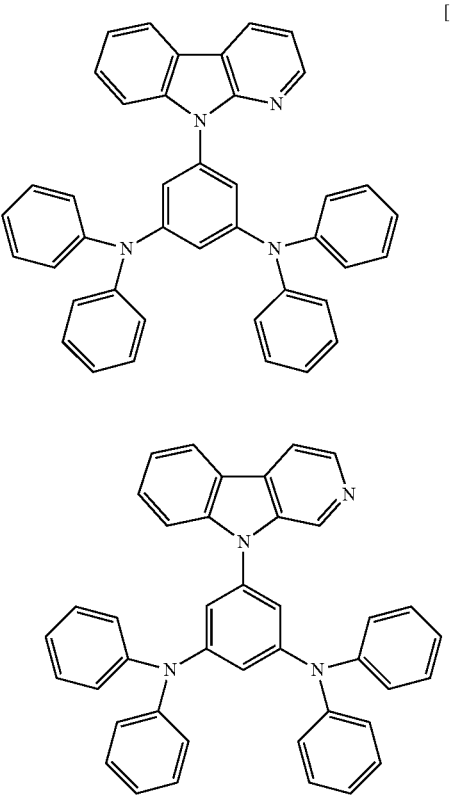

The phosphorescent compound represented by

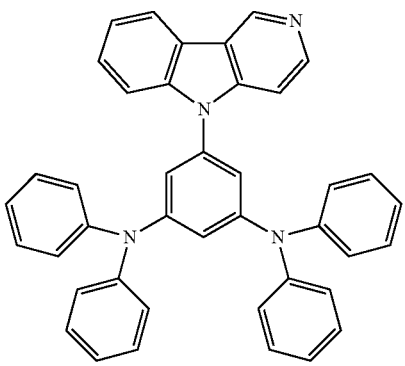 [SMILES: c1ccc(N(c2ccccc2)c2cc(N(c3ccccc3)c3ccccc3)cc(-n3c4ccccc4c4cnccc43)c2)cc1]

in the above Formula 4 is synthesized by following synthesis.

Synthesis of N-(3,5-dibromophenyl)-γ-carboline

N-(3,5-dibromophenyl)-γ-carboline is synthesized by following Reaction Formula 3.

[Reaction Formula 3]

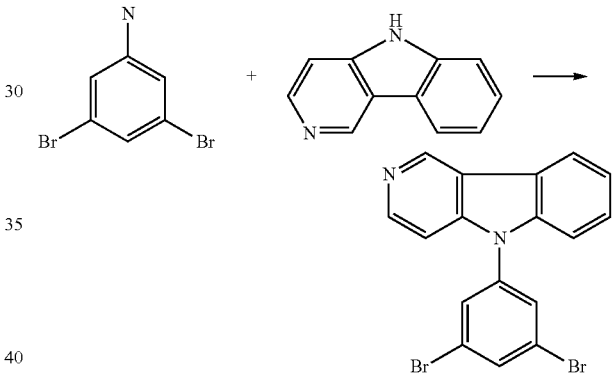

1,3-dibromo-5-iodobenzene 5 g (13.8 mmol), γ-carboline 2.33 g (13.8 mmol), dioxane 50 ml, CuI 0.2 g, trans-diaminocyclohexene 0.7 ml and K$_3$PO$_4$ 6 g are put in a 100 ml two-neck flask and refluxed for 12 hours. After completion of the reaction, the reaction mixture is filtered to remove a salt and water 50 ml are added in the solution to precipitate. The resulting solution is filtered by colum chromatrography with ethylene acetate such that white powder 3.0 g is obtained. (yield: 54%)

2. Synthesis of the Phosphorescent Compound

The phosphorescent compound is synthesized by following Reaction Formula 4.

[Reaction Formula 4]

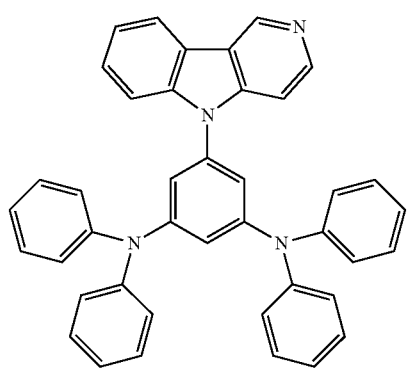

+

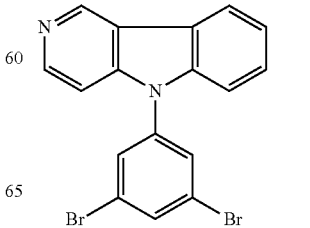

-continued

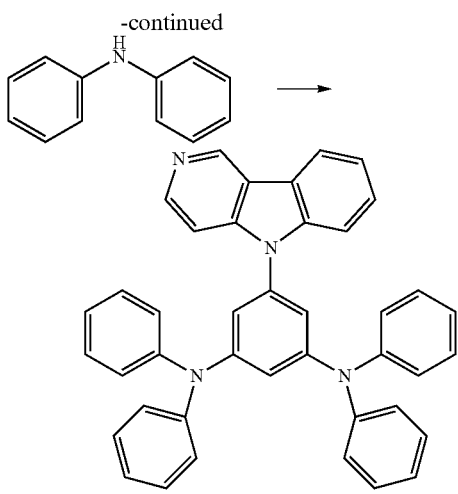

N-(3,5-dibromophenyl)-γ-carboline 2 g (5 mmol), diphenylamine 1.87 g (11 mmol), toluene 50 ml, Pd$_2$(dba)$_3$ 0.1 g, xantphos 0.23 g and sodium-tert-butoxide 1.3 g are put in a 100 ml two-neck flask and refluxed for 12 hours. After completion of the reaction, the solvent is removed, and the resulting residence is washed with water 50 ml. The resulting solution is filtered by colum chromatrography with acetone and hexane of 1:3 such that white powder 1.1 g is obtained. (yield: 75%)

Figure 2A:
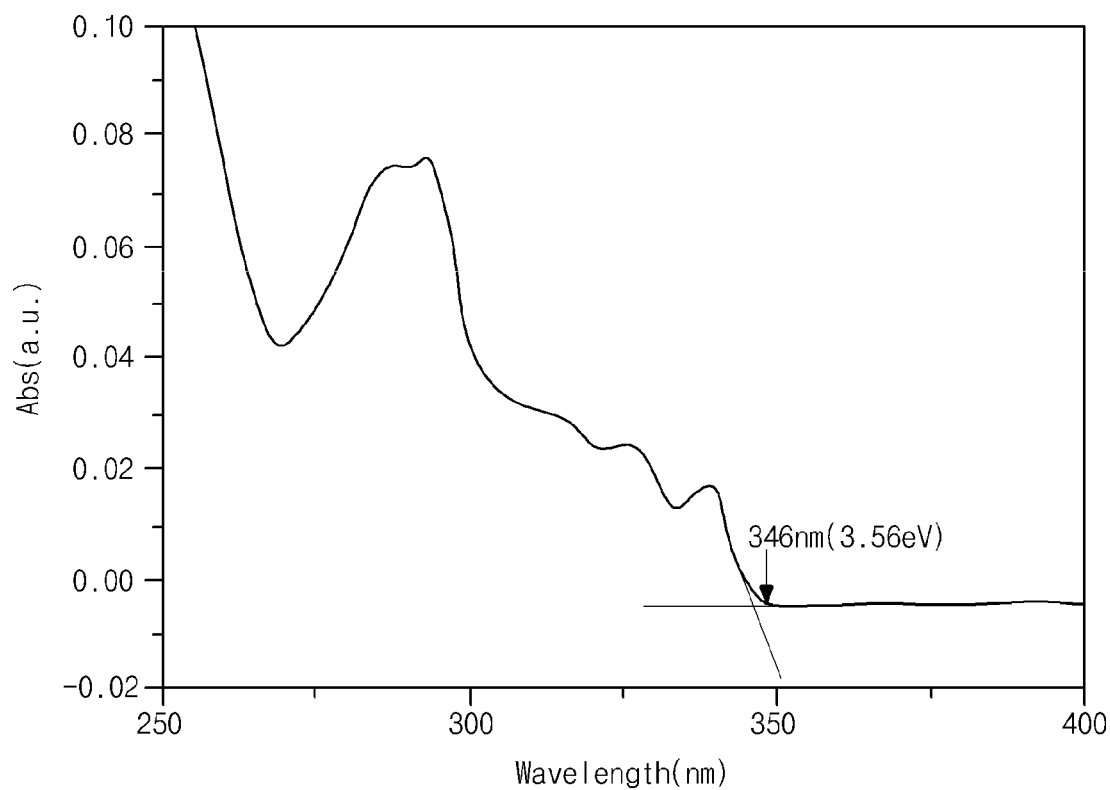
FIGS. 2A and 2B show a UV spectrum and a PL spectrum of a phosphorescent compound according to the first embodiment of the present invention.
Figure 2B:
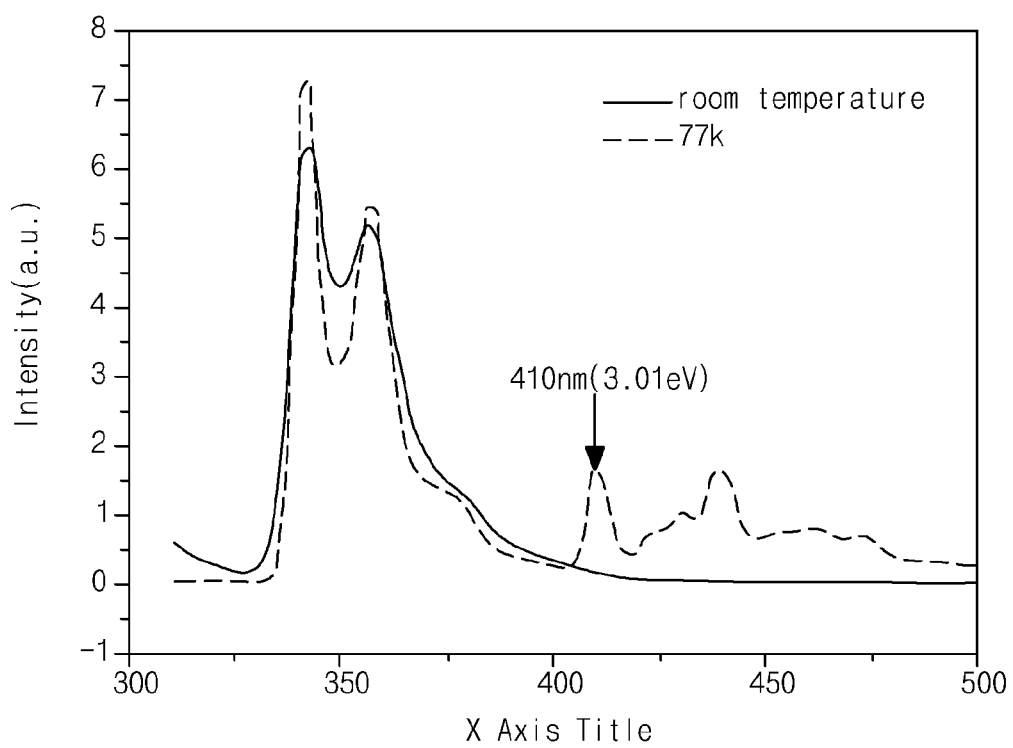

FIGS. 2A and 2B respectively show a UV spectrum and a photoluminescence (PL) spectrum of the phosphorescent compound represented by

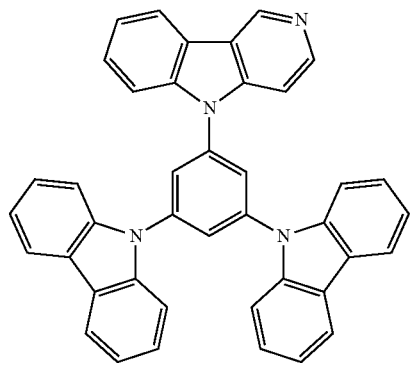 [SMILES: c1ccc2c(c1)c1ccccc1n2-c1cc(-n2c3ccccc3c3ccccc32)cc(-n2c3ccccc3c3cnccc32)c1]

in Formula 2.

Figure 3B:
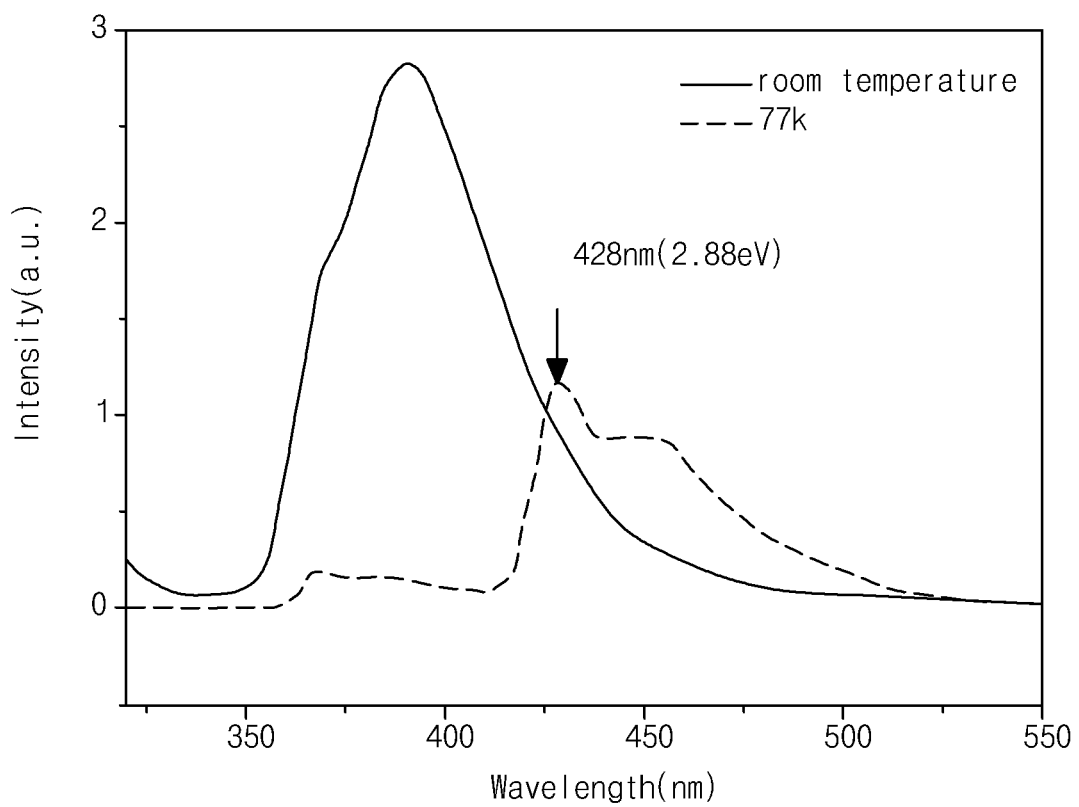

FIGS. 3A and 3B respectively show a UV spectrum and a photoluminescence (PL) spectrum of the phosphorescent compound represented by

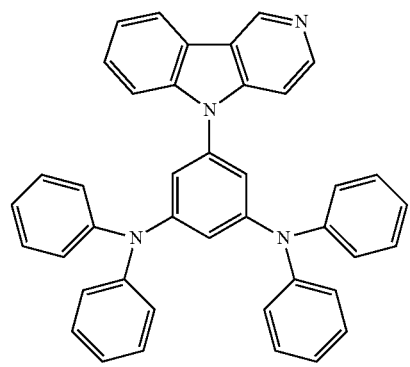 [SMILES: c1ccc(N(c2ccccc2)c2cc(N(c3ccccc3)c3ccccc3)cc(-n3c4ccccc4c4cnccc43)c2)cc1]

in Formula 4.

As shown in FIGS. 2A, 2B, 3A and 3B, the phosphorescent compounds in the first and second embodiments of the present invention has a triplet energy above 2.8 eV and a singlet energy above 3.3 eV. A triplet energy of the phosphorescent compounds in the present invention is larger than that of the related art compound, i.e., CBP, and that of the related art phosphorescent dopant. Accordingly, an energy counter-transition from the dopant to the host is prevented such that an emission yield is improved.

In addition, since the phosphorescent compound in the first and second embodiments of the present invention has the triplet energy larger than the dopant, the phosphorescent compound can be used for the hole transporting layer or the electron transporting layer. An energy counter-transition from the dopant to the hole transporting layer or the electron transporting layer is also prevented.

Figure 4:
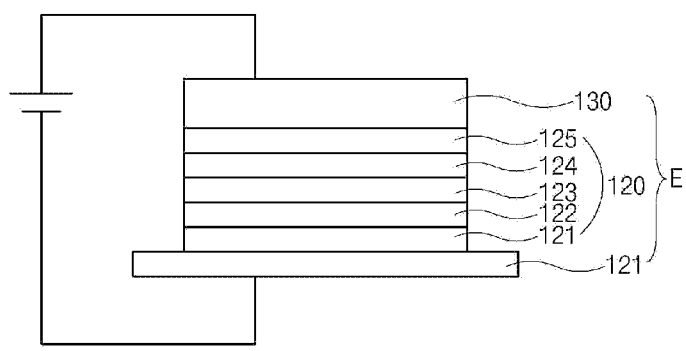
FIG. 4 is a schematic cross-sectional view of an OELD according to the present invention.

Referring to FIG. 4, which is a schematic cross-sectional view of an OELD according to the present invention, the OELD includes a first substrate (not shown), a second substrate (not shown) and an organic electroluminescent diode E between the first and second substrates.

The organic electroluminescent diode E includes a first electrode 110, a second electrode 130 and an organic emitting layer 120. The first electrode 110 is formed of a material having a relatively high work function to serve as an anode. For example, the first electrode 110 may be formed of indium-tin-oxide (ITO). The second electrode 130 is formed of a material having a relatively low work function to serve as a cathode. For example, the second electrode 130 may be formed of aluminum (Al) or Al alloy.

The organic emitting layer 120 includes red, green and blue organic emitting pattern. To increase an emission efficiency, the organic emitting layer 120 includes a hole injection layer (HTL) 121, a hole transporting layer (HIL) 122, an emitting material layer (EML) 123, an electron transporting layer (ETL) 124 and an electron injection layer (EIL) 125.

At least one of the emitting material layer 123, the hole transporting layer 122 and the electron transporting layer 124 includes the phosphorescent compound in the above Formula 1 or the above Formula 3.

For example, when the emitting material layer 123 includes the phosphorescent compound in the above Formula 1 or the above Formula 3 as a host, a dopant is doped with a weight % of about 1 to 10. Since the phosphorescent compound as the host has the triplet energy larger than the dopant, an energy counter-transition from the dopant to the host is prevented. As a result, an emission efficiency is improved. For example, the dopant may be iridium-bis(4,6-difluorophenylpyridineato-N,C2)-picolinate (FIrpic).

On the other hand, when the hole transporting layer 122 and/or the electron transporting layer 124 includes the phosphorescent compound in the above Formula 1 or the above Formula 3, an energy counter-transition from the dopant to the hole transporting layer 122 and/or the electron transporting layer 124 is prevented because a triplet energy of the phosphorescent compound is larger than that of the dopant. Accordingly, the OELD has an improved energy efficiency.

—Third Embodiment—

A phosphorescent compound according to the third embodiment of the present invention includes a structure of tri-phenyl amine derivatives represented by following Formula 5. Namely, carboline or carbazole is substituted at a meta-position of tri-phenyl amine.

[Formula 5]

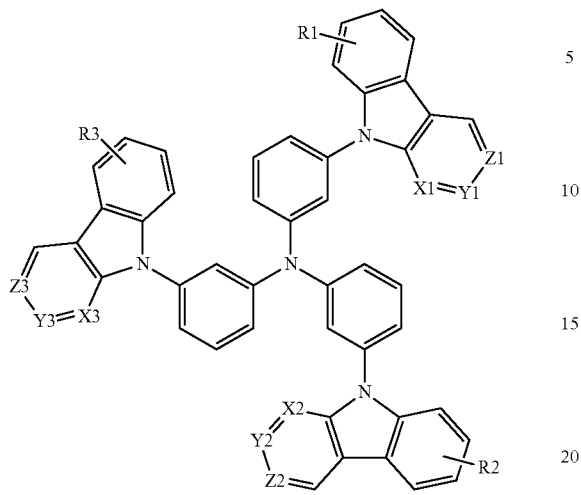

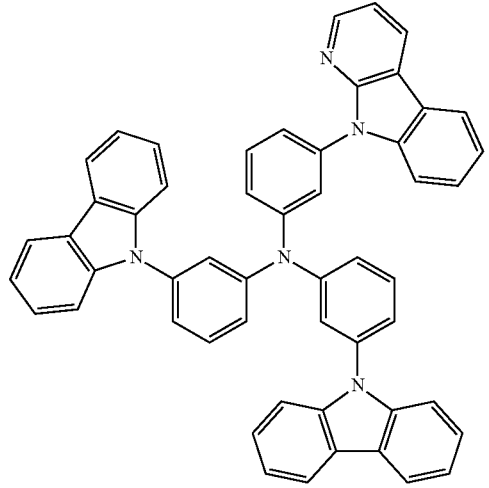

In the above Formula 5, each of X1, X2, X3, Y1, Y2, Y3, Z1, Z2 and Z3 is one of carbon and nitrogen. For example, when all of X1, Y1 and Z1 are carbon, the substituted group is carbazole. When X1 is nitrogen and both of Y1 and Z1 are carbon, the substituted group is carboline referred to as α-carboline. When Y1 is nitrogen and both of X1 and Z1 are carbon, carboline is referred to as β-carboline. When Z1 is nitrogen and both of X1 and Y1 are carbon, carboline is referred to as γ-carboline.

In addition, in the above Formula 5, each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20, such as phenyl, naphthyl, biphenyl, terphenyl and phenanthrenyl.

The phosphorescent compound in Formula 5 is one of compounds in following Formula 6.

[Formula 6]

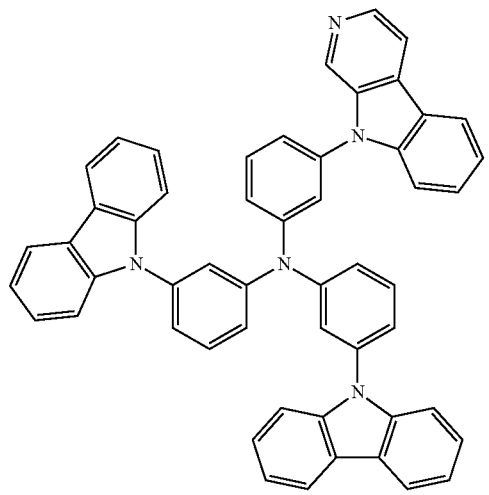

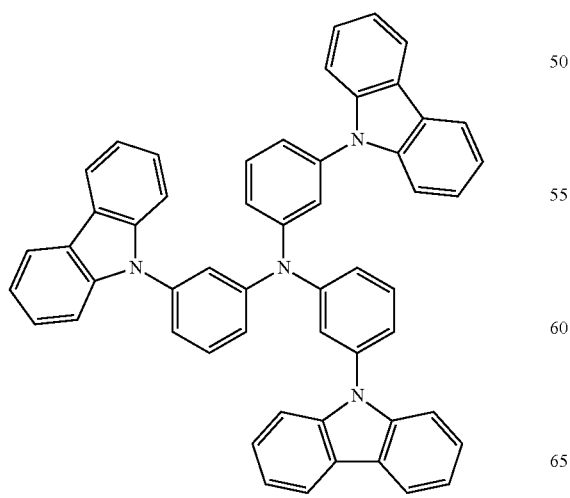

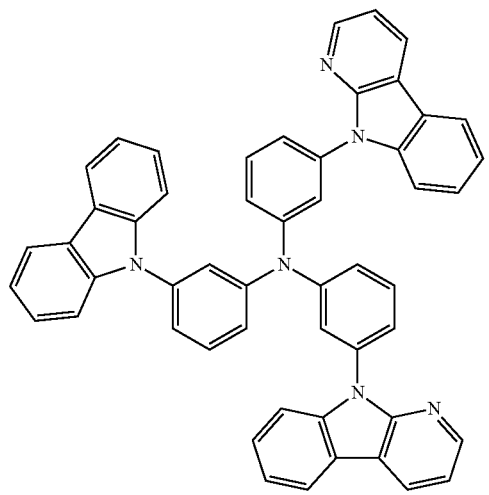

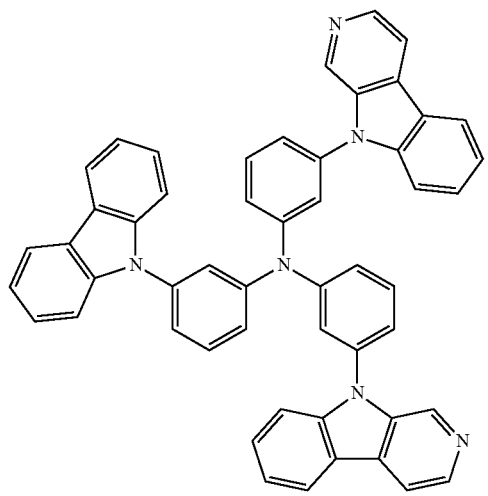
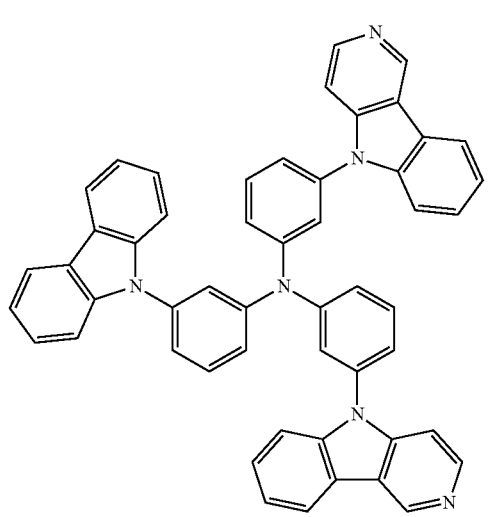
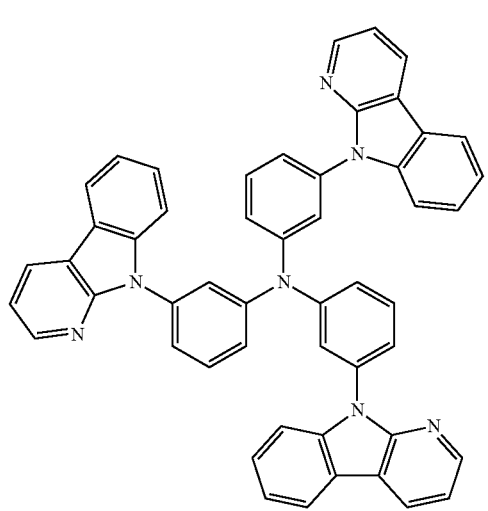
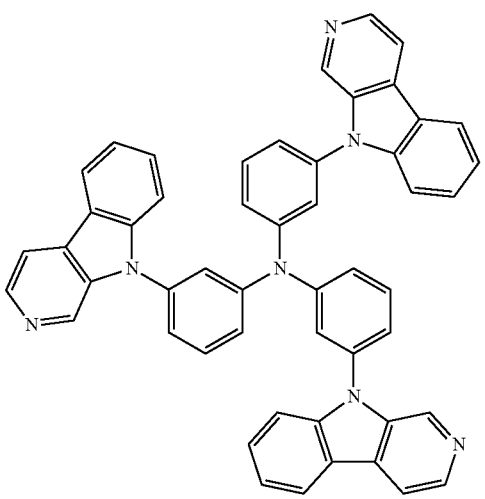
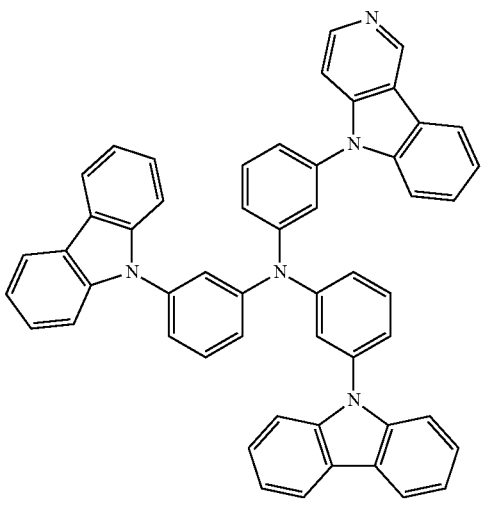 [SMILES: c1cc(N(c2cccc(-n3c4ccccc4c4ccccc43)c2)c2cccc(-n3c4ccccc4c4cnccc43)c2)cc(-n2c3ccccc3c3ccccc32)c1]
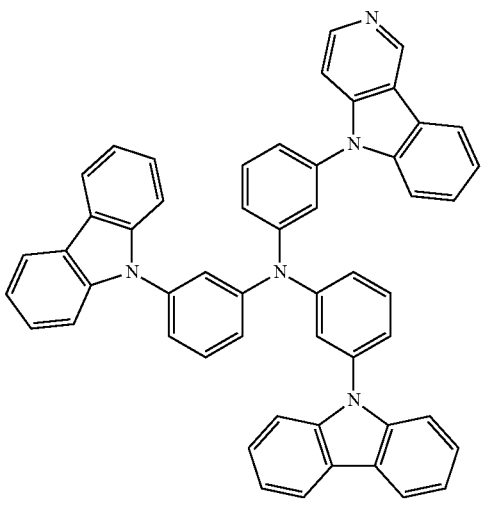 [SMILES: c1cc(N(c2cccc(-n3c4ccccc4c4ccccc43)c2)c2cccc(-n3c4ccccc4c4cnccc43)c2)cc(-n2c3ccccc3c3ccccc32)c1]

The phosphorescent compound of 3,3',3''-(N-carbazolyl)-triphenylamine (mTCTA) represented by

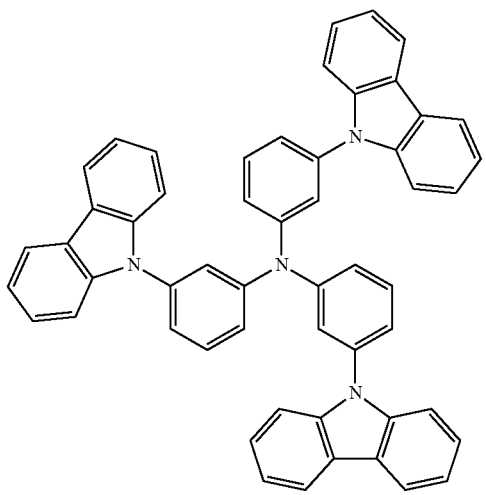 [SMILES: c1cc(N(c2cccc(-n3c4ccccc4c4ccccc43)c2)c2cccc(-n3c4ccccc4c4ccccc43)c2)cc(-n2c3ccccc3c3ccccc32)c1]

in the above Formula 6 is synthesized by following synthesis.

[Reaction Formula 5]

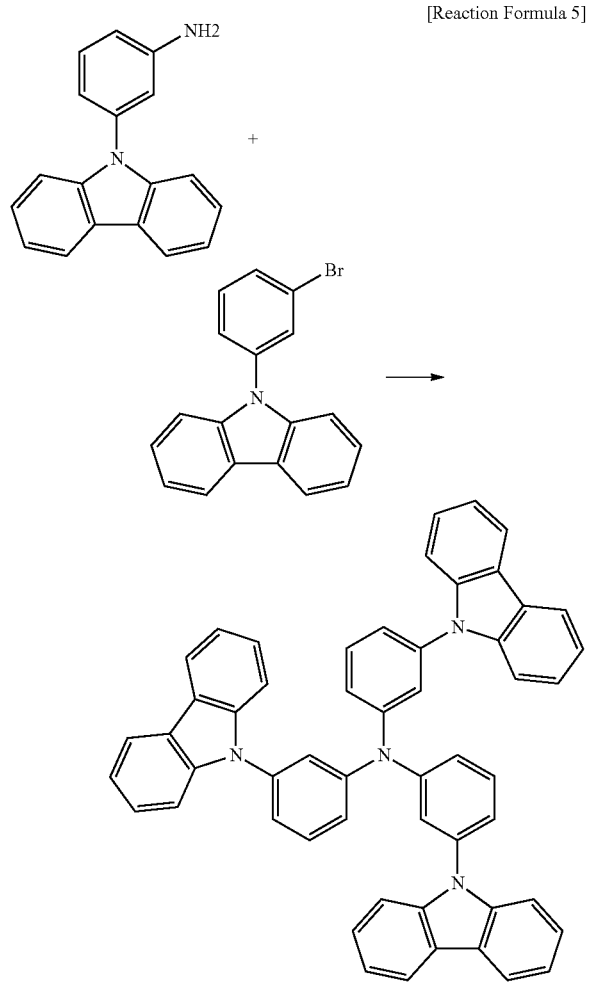

3-(N-carbazolyl)benzenamine 1.5 g (5.8 mmol), N-(3-bromophenyl)-α-carbazole 4.0 g (12.3 mmol), toluene 50 ml, sodium-tert-butoxide 2.2 g (23 mmol), Pd2(dba)3 0.3 g (0.3 mmol), and tris-tert-butylphosphine 0.4 g (2 mmol) are put in a 100 ml two-neck flask and refluxed for 12 hours under a condition of nitrogen. After completion of the reaction, the reaction mixture is cooled into a room temperature and toluene is removed. Sediment is obtained in methanol 100 ml. The resulting solution is filtered by colum chromatrography with methylenchloride and hexane of 1:3 such that white powder 3.2 g is obtained. (yield: 77%)

The phosphorescent compound of 3,3'-di(N-α-carbolinyl)-3''-(N-carbazolyl)-triphenylamine (mDACTA) represented by

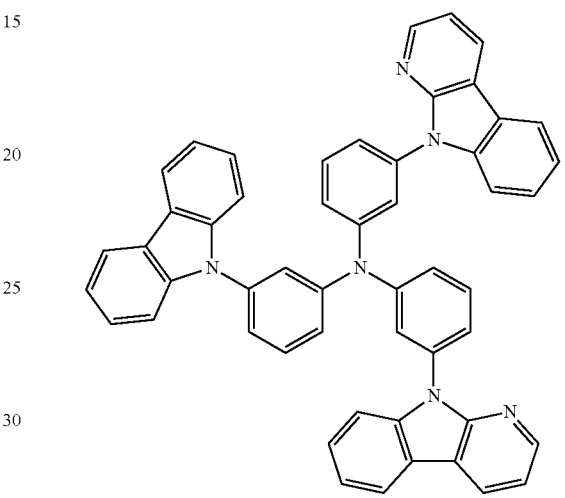

in the above Formula 6 is synthesized by following synthesis.

1. Synthesis of N-(3-bromophenyl)-α-carboline

N-(3-bromophenyl)-α-carboline is synthesized by following Reaction Formula 6.

[Reaction Formula 6]

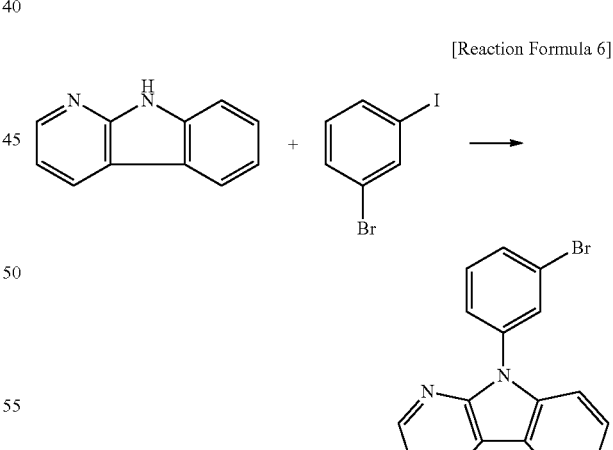

α-carboline 7.3 g (43.4 mmol), 3-iodo-bromobenzene 13.6 g (48 mmol), CuI 0.58 g, 1,2-cyclohexyldiamine 0.68 g, $K_3PO_4$ 18.4 g and dioxane 100 ml are put in a 250 ml two-neck flask and refluxed for 12 hours. The solution is filtered and extracted. Then, the solid is dissolved with methylene chloride, and the resulting residence is filtered by silicagel chromatography such that solid 8.4 g is obtained. (yield: 60%)

2. Synthesis of 3,3'-di(N-α-carbolinyl)-3"-(N-carbazolyl)-triphenylamine 3,3'-di(N-α-carbolinyl)-3"-(N-carbazolyl)-triphenylamine is synthesized by following Reaction Formula 7.

[Reaction Formula 7]

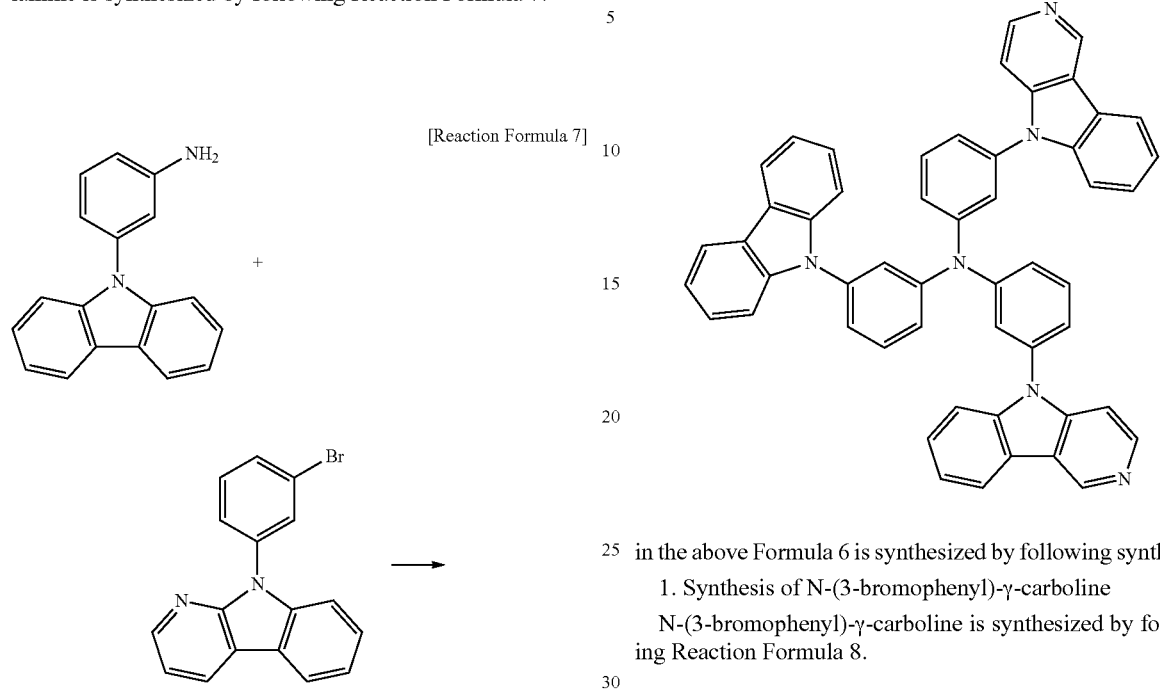

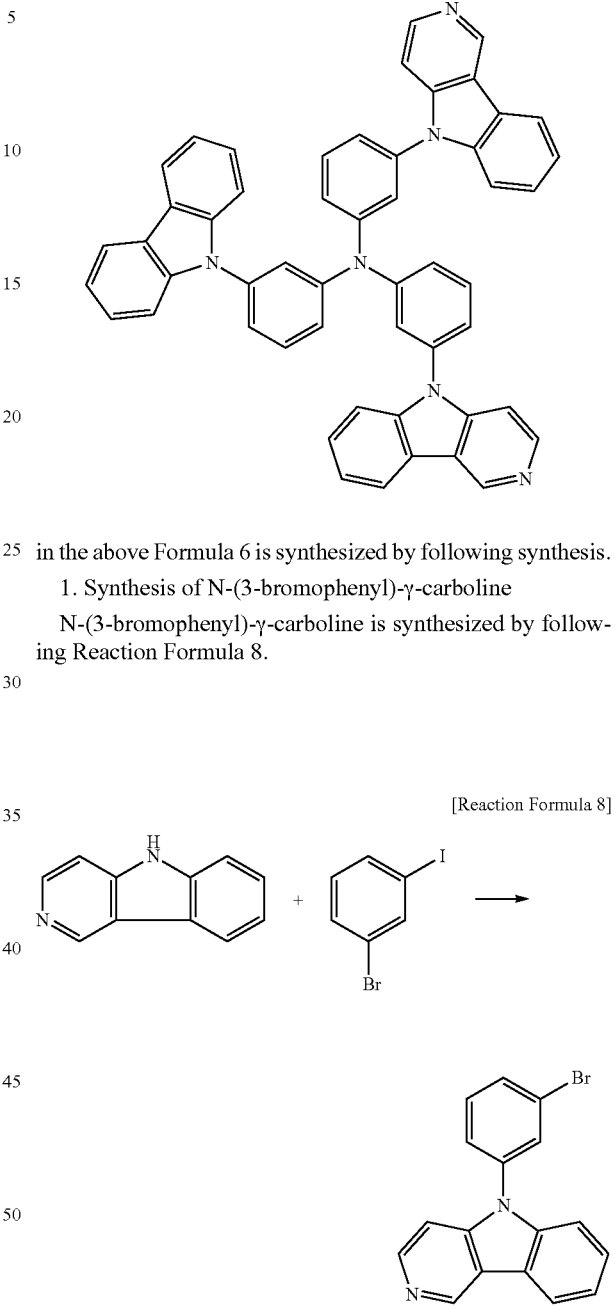

3-(N-carbazolyl)benzenamine 1.5 g (5.8 mmol), N-(3-bromophenyl)-α-carboline 4.0 g (12.3 mmol), toluene 50 ml, sodium-tert-butoxide 2.2 g (23 mmol), Pd2(dba)3 0.3 g (0.3 mmol), and tris-tert-butylphosphine 0.4 g (2 mmol) are put in a 100 ml two-neck flask and refluxed for 12 hours under a condition of nitrogen. After completion of the reaction, the reaction mixture is cooled into a room temperature and toluene is removed. Methanol 100 ml is added and cooled into a 0° C. The resulting solution is filtered. The resulting residence is filtered by colum chromatography with acetone and hexane of 1:2 such that white powder 3.4 g is obtained. (yield: 81%)

The phosphorescent compound of 3,3'-di(N-γ-carbolinyl)-3"-(N-carbazolyl)-triphenylamine (mDGCTA) represented by in the above Formula 6 is synthesized by following synthesis.

1. Synthesis of N-(3-bromophenyl)-γ-carboline

N-(3-bromophenyl)-γ-carboline is synthesized by following Reaction Formula 8.

[Reaction Formula 8]

γ-carboline 4 g (23.8 mmol), 4-iodo-bromobenzene 8.1 g (28.5 mmol), CuI 0.58 g, 1,2-cyclohexyldiamine 0.68 g, K₃PO₄ 12.6 g and dioxane 100 ml are put in a 250 ml two-neck flask and refluxed for 12 hours. The solution is filtered and extracted. Then, the solid is dissolved with ethylacetate, and the resulting residence is filtered by silicagel chromatography such that solid 5.0 g is obtained. (yield: 86%)

2. Synthesis of 3,3'-di(N-γ-carbolinyl)-3"-(N-carbazolyl)-triphenylamine 3,3'-di(N-γ-carbolinyl)-3"-(N-carbazolyl)-triphenylamine is synthesized by following Reaction Formula 9.

[Reaction Formula 9]

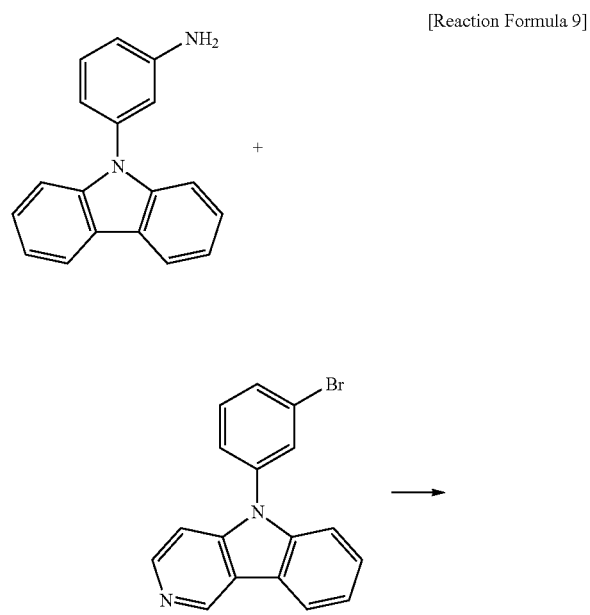

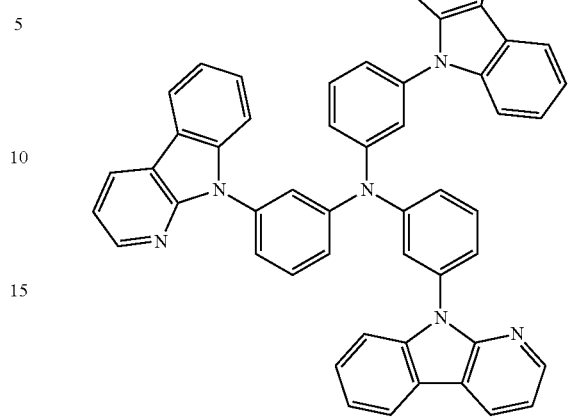

in the above Formula 6 is synthesized by following synthesis.

1. Synthesis of N-(3-bromophenyl)-α-carboline

N-(3-bromophenyl)-α-carboline is synthesized by following Reaction Formula 10.

[Reaction Formula 10]

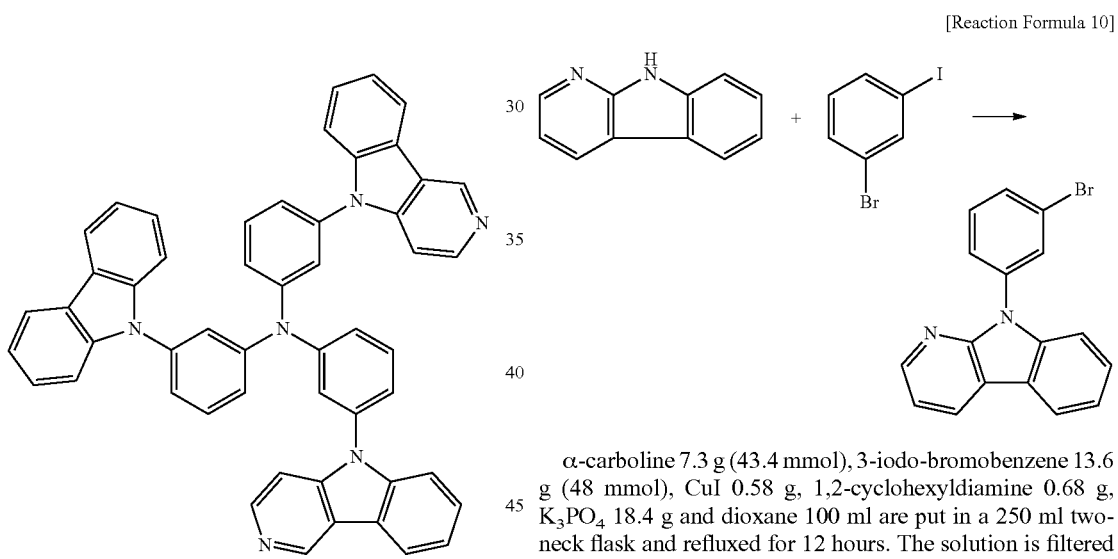

α-carboline 7.3 g (43.4 mmol), 3-iodo-bromobenzene 13.6 g (48 mmol), CuI 0.58 g, 1,2-cyclohexyldiamine 0.68 g, $K_3PO_4$ 18.4 g and dioxane 100 ml are put in a 250 ml two-neck flask and refluxed for 12 hours. The solution is filtered and extracted. Then, the solid is dissolved with methylene chloride, and the resulting residence is filtered by silicagel chromatography such that solid 8.4 g is obtained. (yield: 60%)

2. Synthesis of 3,3',3"-(N-α-carbolinyl)-triphenylamine 3,3',3"-(N-α-carbolinyl)-triphenylamine is synthesized by following Reaction Formula 11.

3-(N-carbazolyl)benzenamine 1.5 g (5.8 mmol), N-(3-bromophenyl)-γ-carboline 4.0 g (12.3 mmol), toluene 50 ml, sodium-tert-butoxide 2.2 g (23 mmol), Pd2(dba)3 0.15 g, and 1,1'-bis(diphenylphosphino)-ferrocene 0.2 g are put in a 100 ml two-neck flask and refluxed for 12 hours under a condition of nitrogen. After completion of the reaction, the reaction mixture is cooled into a room temperature and toluene is removed. Methanol 100 ml is added and is filtered. The resulting residence is filtered by colum chromatrography with tetrahydrofuran (THF) such that white powder 2.2 g is obtained. (yield: 53%)

The phosphorescent compound of 3,3',3"-(N-α-carbolinyl)-triphenylamine (mTATA) represented by

[Reaction Formula 11]

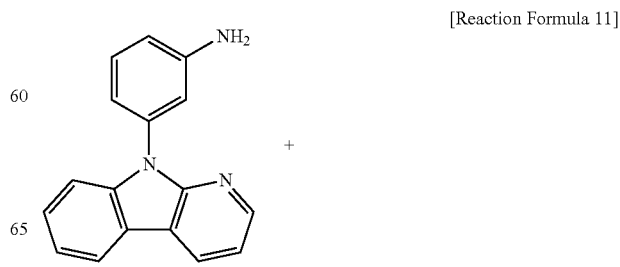

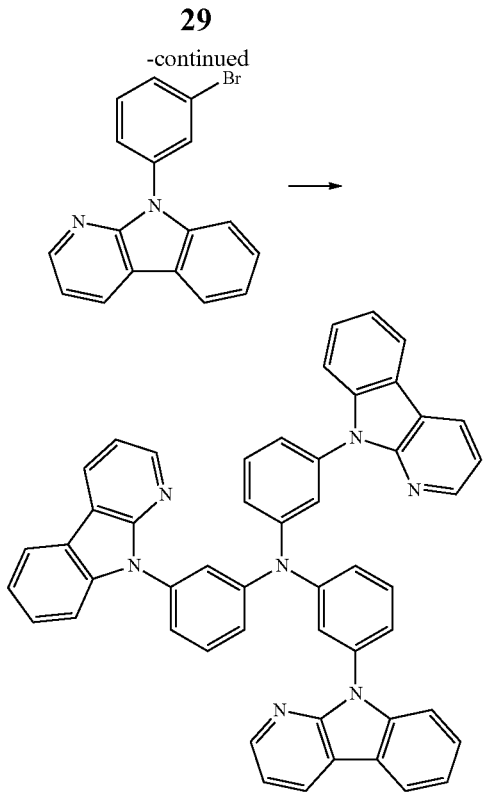

3-(N-α-carbazolyl)benzenamine 1.5 g (5.8 mmol), N-(3-bromophenyl)-α-carboline 4.0 g (12.3 mmol), toluene 50 ml, sodium-tert-butoxide 2.2 g (23 mmol), Pd2(dba)3 0.3 g 0.3 mmol), and tris-tert-bytylphosphine 0.4 g (2 mmol) are put in a 100 ml two-neck flask and refluxed for 12 hours under a condition of nitrogen. After completion of the reaction, the reaction mixture is cooled into a room temperature and toluene is removed. Methanol 100 ml is added and cooled into a 0° C. The resulting solution is filtered. The resulting residence is filtered by colum chromatrography with acetone and hexane of 1:2 such that white powder 3.5 g is obtained. (yield: 84%)

Figure 5A:
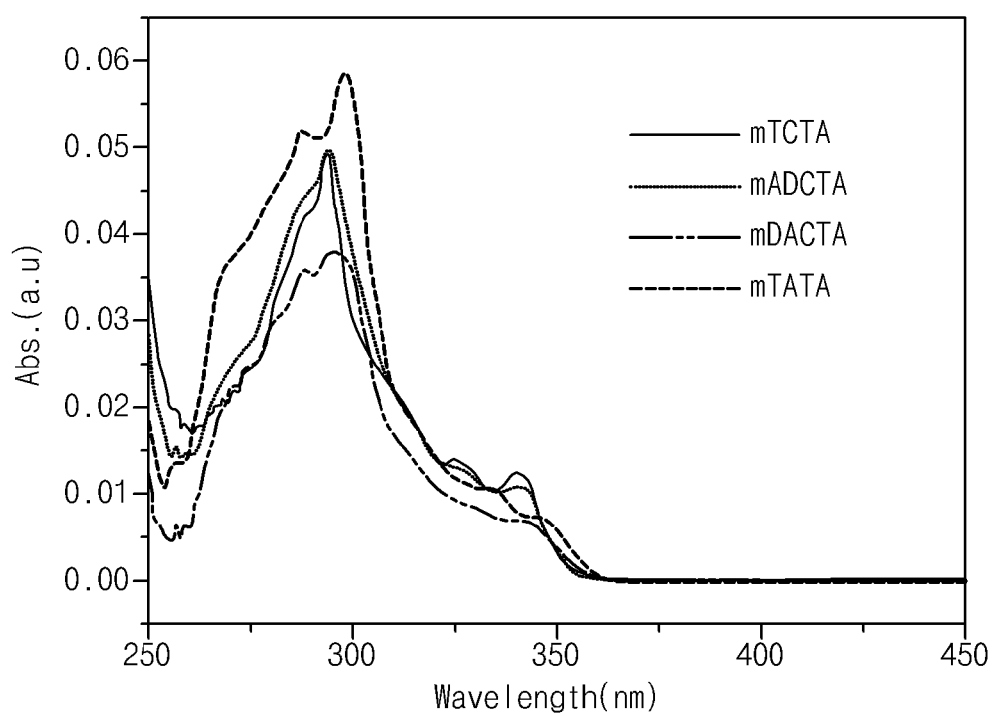
FIGS. 5A and 5B show UV spectrums and PL spectrums of phosphorescent compounds according to the third embodiment of the present invention.
Figure 5B:
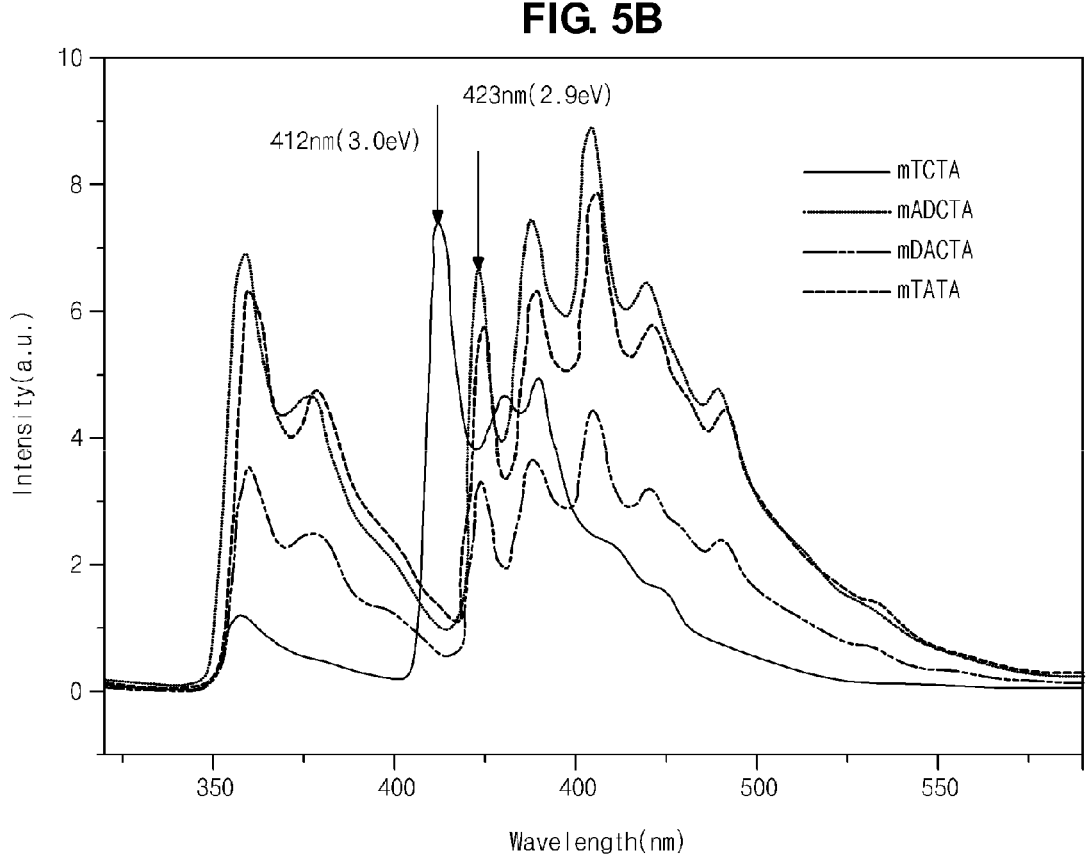

FIGS. 5A and 5B show UV spectrums and PL spectrums of phosphorescent compounds in the third embodiment of the present invention. As shown in FIGS. 5A and 5B, the phosphorescent compounds according to the third embodiment of the present invention have a triplet energy above 2.8 eV. A triplet energy of the phosphorescent compounds in the present invention is larger than that of the related art compound, i.e., CBP, and that of the related art phosphorescent dopant. Accordingly, an energy counter-transition from the dopant to the host is prevented such that an emission yield is improved.

In addition, since the phosphorescent compound in the third embodiment of the present invention has the triplet energy larger than the dopant, the phosphorescent compound can be used for the hole transporting layer or the electron transporting layer. An energy counter-transition from the dopant to the hole transporting layer or the electron transporting layer is also prevented.

Furthermore, since the phosphorescent compound has an excellent solubility, the device can be formed by a coating process. Namely, the related art phosphorescent compound, i.e., CBP, has low solubility such that the device is formed by a deposition process. However, since phosphorescent compound has an excellent solubility, the device can be formed by a coating process such that a fabrication process is simplified and production cost is reduced.

Referring again FIG. 4, the OELD includes a first substrate (not shown), a second substrate (not shown) and an organic electroluminescent diode E between the first and second substrates.

The organic electroluminescent diode E includes a first electrode 110, a second electrode 130 and an organic emitting layer 120. The first electrode 110 is formed of a material having a relatively high work function to serve as an anode. For example, the first electrode 110 may be formed of indium-tin-oxide (ITO). The second electrode 130 is formed of a material having a relatively low work function to serve as a cathode. For example, the second electrode 130 may be formed of aluminum (Al) or Al alloy.

The organic emitting layer 120 includes red, green and blue organic emitting pattern. To increase an emission efficiency, the organic emitting layer 120 includes a hole injection layer (HTL) 121, a hole transporting layer (HIL) 122, an emitting material layer (EML) 123, an electron transporting layer (ETL) 124 and an electron injection layer (EIL) 125.

At least one of the emitting material layer 123, the hole transporting layer 122 and the electron transporting layer 124 includes the phosphorescent compound in the above Formula 5.

For example, when the emitting material layer 123 includes the phosphorescent compound in the above Formula 5 as a host, a dopant is doped with a weight % of about 1 to 10. Since the phosphorescent compound as the host has the triplet energy larger than the dopant, an energy counter-transition from the dopant to the host is prevented. As a result, an emission efficiency is improved. For example, the dopant may be iridium-bis(4,6-difluorophenylpyridineato-N,C2)-picolinate (FIrpic).

On the other hand, when the hole transporting layer 122 and/or the electron transporting layer 124 includes the phosphorescent compound in the above Formula 5, an energy counter-transition from the dopant to the hole transporting layer 122 and/or the electron transporting layer 124 is prevented because a triplet energy of the phosphorescent compound is larger than that of the dopant.

In addition, since the phosphorescent compound in the third embodiment has an excellent solubility, the device can be fabricated by a coating process. As a result, a fabricating process is simplified and production cost is reduced.

—Fourth Embodiment—

A phosphorescent compound according to the fourth embodiment of the present invention includes a structure of tri-phenyl amine derivatives represented by following Formula 7. Namely, three carboline groups are substituted at a para-position of tri-phenyl amine.

[Formula 7]

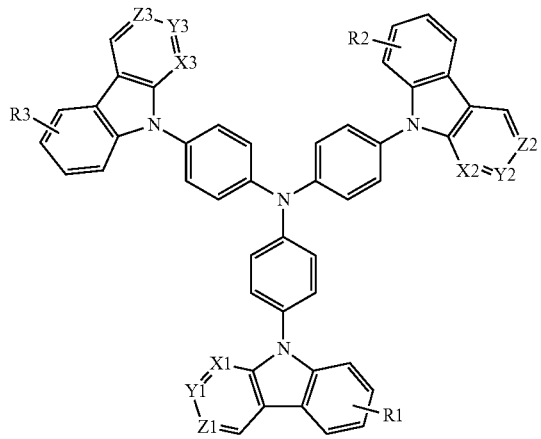

In the above Formula 7, each of X1, X2, X3, Y1, Y2, Y3, Z1, Z2 and Z3 is one of carbon and nitrogen, and at least one of X1, X2, X3, Y1, Y2, Y3, Z1, Z2 and Z3 is nitrogen. For example, when X1 is nitrogen and both of Y1 and Z1 are carbon, carboline is referred to as α-carboline. When Y1 is nitrogen and both of X1 and Z1 are carbon, carboline is referred to as β-carboline. When Z1 is nitrogen and both of X1 and Y1 are carbon, carboline is referred to as γ-carboline.

In addition, in the above Formula 7, each of R1, R2 and R3 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formula 7 is one of compounds in following Formula 8.

[Formula 8]

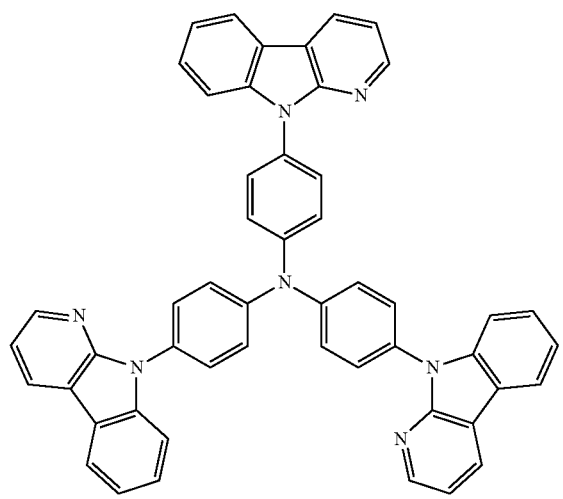

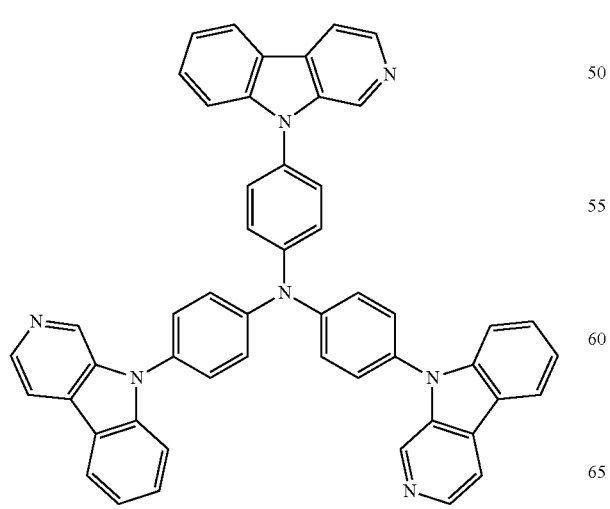

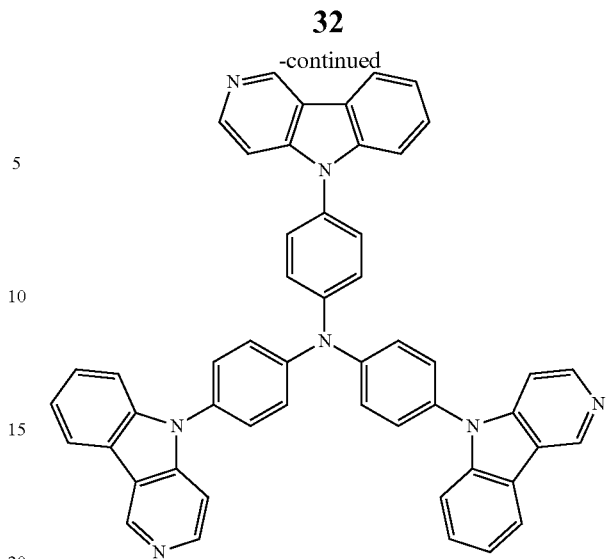

The phosphorescent compound represented by

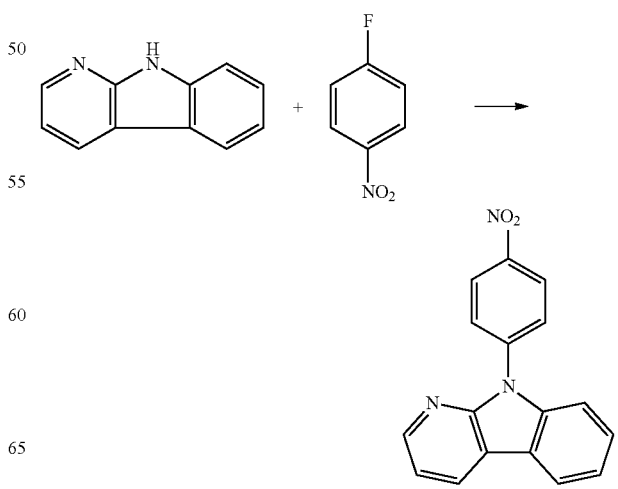

in the above Formula 8 is synthesized by following synthesis.
1. Synthesis of N-(4-nitrophenyl)-α-carboline
N-(4-nitrophenyl)-α-carboline is synthesized by following Reaction Formula 12.

[Reaction Formula 12]

α-carboline 10 g (60 mmol), 4-fluoronitrobenzene 8.6 g (61 mol), NaH 1.58 g (66 mmol) and DMF 100 ml are put in a 250 ml two-neck flask and refluxed for 12 hours. After completion of the reaction, the reaction mixture is precipitated by adding 100 ml water and filtered such that 17.4 g solid is obtained. (57%)

2. Synthesis of 4-(N-α-carbazolyl)benzenamine 4-(N-α-carbazolyl)benzenamine is synthesized by following Reaction Formula 13.

[Reaction Formula 13]

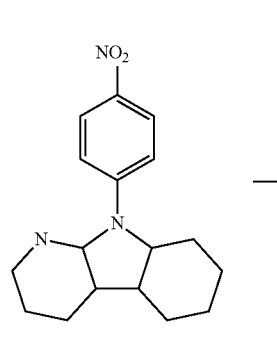 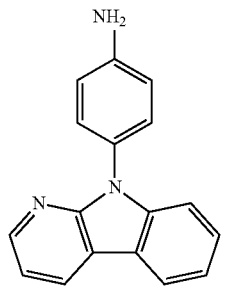

N-(4-nitrophenyl)-α-carboline 7 g (23.8 mmol), SnCl2 16.31 g (72.1 mmol) and ethanol 100 ml are put in a 250 ml two-neck flask and refluxed for 4 hours. After completion of the reaction, the reaction mixture is neutralized by adding NaOH and extracted by using ether. Next, the resulting residence is distilled such that 4-(N-α-carbazolyl)benzenamine 5.2 g is obtained. (84%)

3. Synthesis of N-(4-bromophenyl)-α-carboline

N-(4-bromophenyl)-α-carboline is synthesized by following Reaction Formula 14.

[Reaction Formula 14]

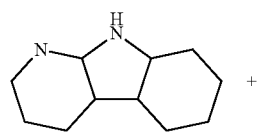 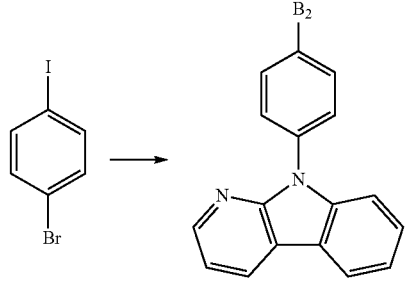

α-carboline 8 g (47.6 mmol), 4-iodo-bromobenzene 20 g (70.6 mol), CuI 0.58 g, 1,2-cyclohexyldiamine 0.68 g, K3PO4 25.4 g and dioxane 150 ml are put in a 250 ml two-neck flask and refluxed for 12 hours. After adding water 150 ml and precipitating, the resulting residence is filtered by silicagel chromatography with methylene chloride such that 9.3 g solid is obtained. (60%)

4. Synthesis of 4,4',4''-(N-α-carbolinyl)-triphenylamine 4,4',4''-(N-α-carbolinyl)-triphenylamine is synthesized by following Reaction Formula 15.

[Reaction Formula 15]

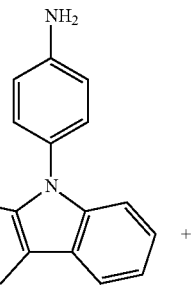 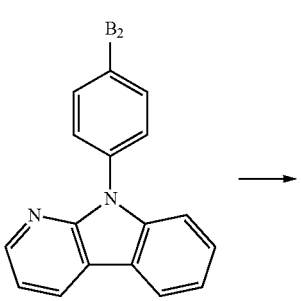

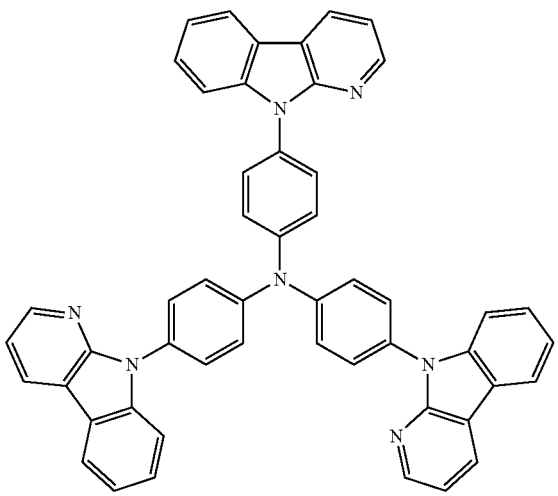

4-(N-α-carbazolyl)benzenamine 2 g (7.7 mmol), N-(4-bromophenyl)-α-carboline 5.5 g (18 mmol), toluene 50 ml, sodium tert-butoxide 2.2 g (23 mmol), Pd2(dba)3 0.3 g (0.3 mmol) and tris-tert-butylphosphine 0.4 g (2 mmol) are put in a 100 ml two-neck flask and refluxed under a condition of nitrogen and for 12 hours. After completion of the reaction, the resulted mixture is cooled to a room temperature and precipitated by adding methanol 100 ml. Then, the mixture is resolved in methylenchloride and absorbed by silicagel. The mixture is filtered by silicagel column chromatography with THF such that white powder 3.4 g is obtained. (yield: 60%)

—Fifth Embodiment—

A phosphorescent compound according to the fifth embodiment of the present invention includes a structure of tri-phenyl amine derivatives represented by following Formula 9. Namely, two carboline groups and one carbazole group are respectively substituted at a para-position of tri-phenyl amine.

[Formula 9]

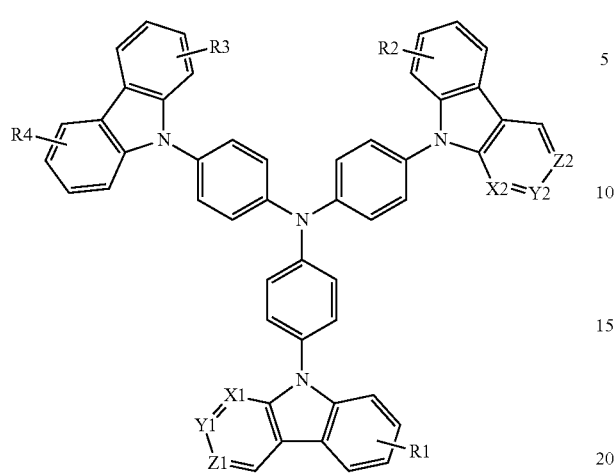

In the above Formula 9, each of X1, X2, Y1, Y2, Z1 and Z2 is one of carbon and nitrogen, and at least one of X1, X2, Y1, Y2, Z1 and Z2 is nitrogen. For example, when X1 is nitrogen and both of Y1 and Z1 are carbon, carboline is referred to as α-carboline. When Y1 is nitrogen and both of X1 and Z1 are carbon, carboline is referred to as β-carboline. When Z1 is nitrogen and both of X1 and Y1 are carbon, carboline is referred to as γ-carboline.

In addition, in the above Formula 9, each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formula 9 is one of compounds in following Formula 10.

[Formula 10]

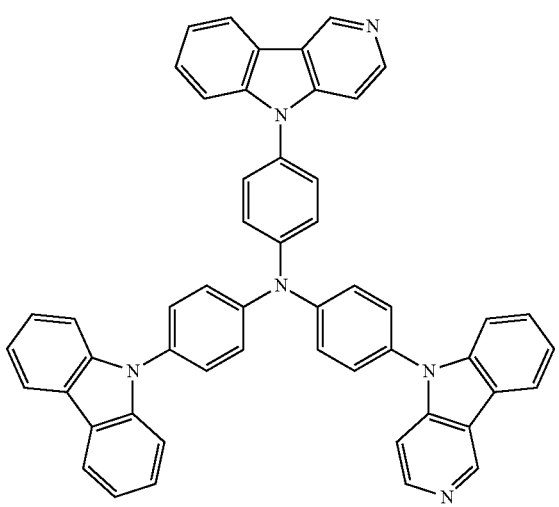

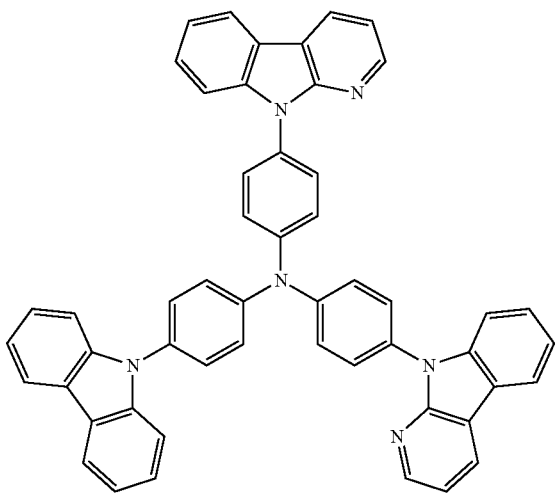

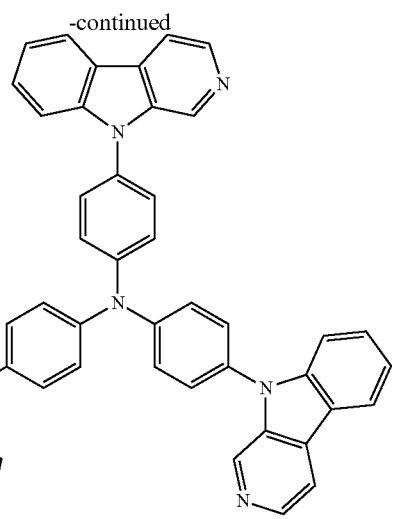

The phosphorescent compound represented by in the above Formula 10 is synthesized by following synthesis.

1. Synthesis of 4,4'-(N-α-carbolinyl)-4''-(N-carbazolyl)-triphenylamine 4,4'-di(N-α-carbolinyl)-4''-(N-carbazolyl)-triphenylamine is synthesized by following Reaction Formula 16.

[Reaction Formula 16]

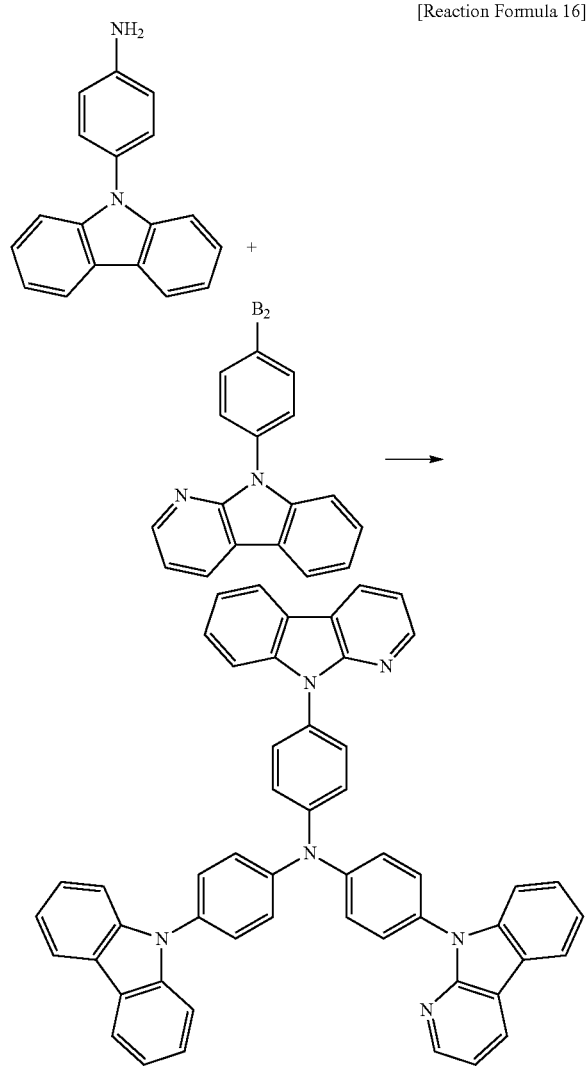

4-(N-carbazolyl)benzenamine 2 g (7.7 mmol), N-(4-bromophenyl)-α-carboline 5.5 g (18 mmol), toluene 50 ml, sodium-tert-butoxide 2.2 g (23 mmol), Pd2(dba)3 0.3 g (0.3 mmol) and tris-tert-butylphosphine 0.4 g (2 mmol) are put in a 100 ml two-neck flask and refluxed under a condition of nitrogen and for 12 hours. After completion of the reaction, the resulted mixture is cooled to a room temperature and precipitated by adding methanol 100 ml. Then, the mixture is resolved in methylenchloride and absorbed by silicagel. The mixture is filtered by silicagel column chromatography with THF such that white powder 3.7 g is obtained. (yield: 65%)

—Sixth Embodiment—

A phosphorescent compound according to the sixth embodiment of the present invention includes a structure of tri-phenyl amine derivatives represented by following Formula 11. Namely, one carboline group and two carbazole groups are respectively substituted at a para-position of tri-phenyl amine.

[Formula 11]

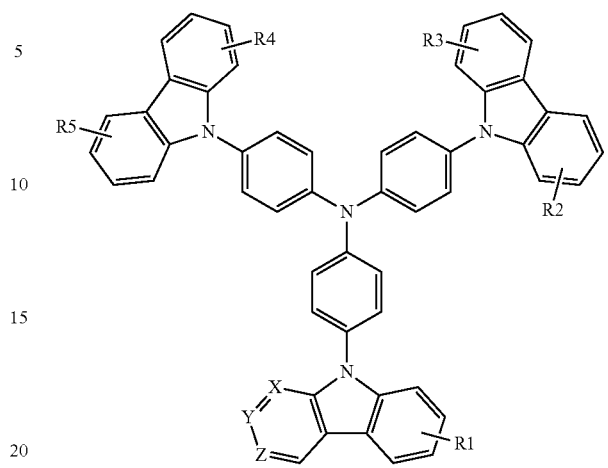

In the above Formula 11, each of X, Y and Z is one of carbon and nitrogen, and at least one of X, Y and Z is nitrogen. For example, when X is nitrogen and both of Y and Z are carbon, carboline is referred to as α-carboline. When Y is nitrogen and both of X and Z are carbon, carboline is referred to as β-carboline. When Z is nitrogen and both of X and Y are carbon, carboline is referred to as γ-carboline.

In addition, in the above Formula 11, each of R1, R2, R3, R4 and R5 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formula 11 is one of compounds in following Formula 12.

[Formula 12]

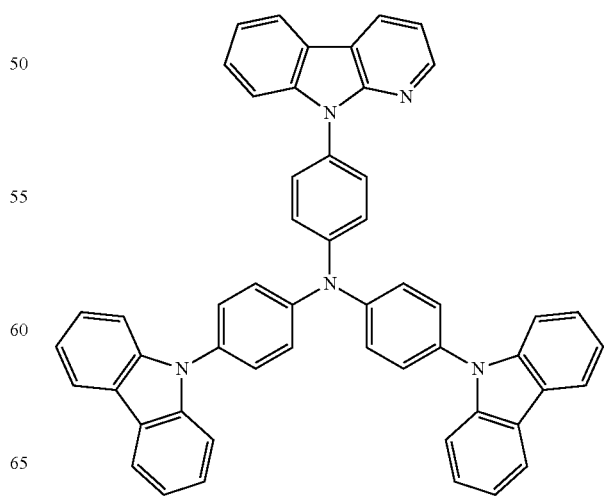

-continued

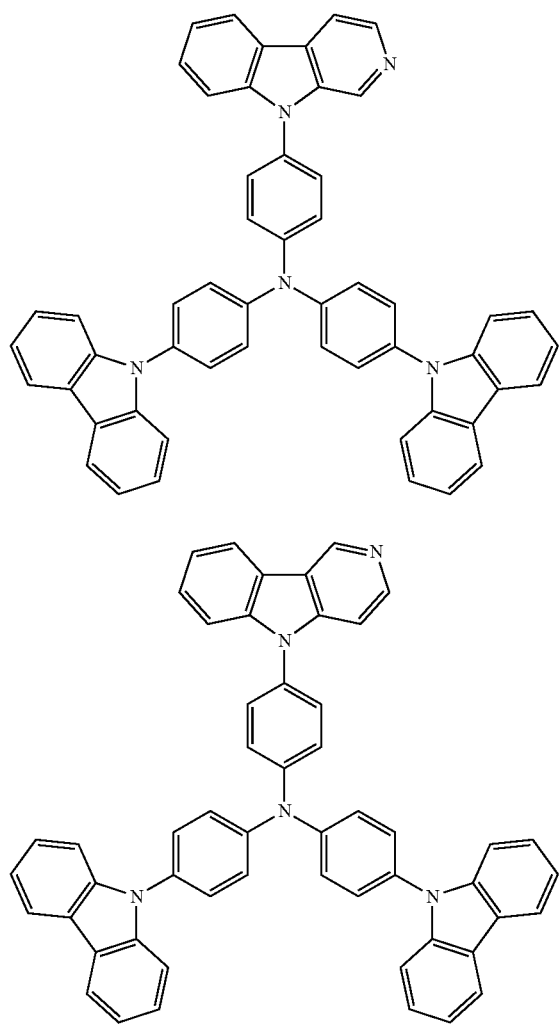

The phosphorescent compound represented by

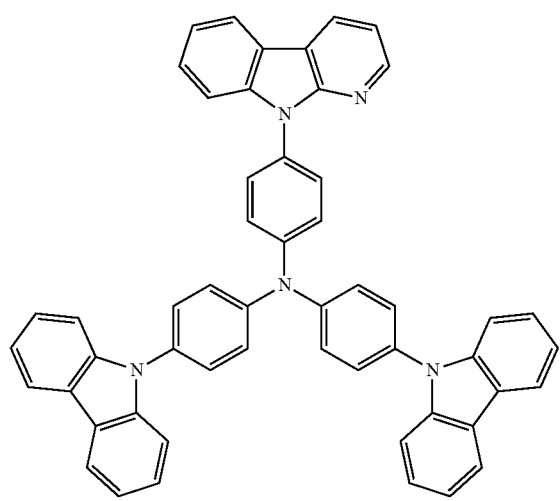 [SMILES: c1ccc2c(c1)c1ccccc1n2-c1ccc(N(c2ccc(-n3c4ccccc4c4ccccc43)cc2)c2ccc(-n3c4ccccc4c4cccnc43)cc2)cc1]

in the above Formula 12 is synthesized by following synthesis.

1. Synthesis of 4-(N-α-carbolinyl)-4',4"-di(N-carbazolyl)-triphenylamine 4-(N-α-carbolinyl)-4',4"-di(N-carbazolyl)-triphenylamine is synthesized by following Reaction Formula 17.

[Reaction Formula 17]

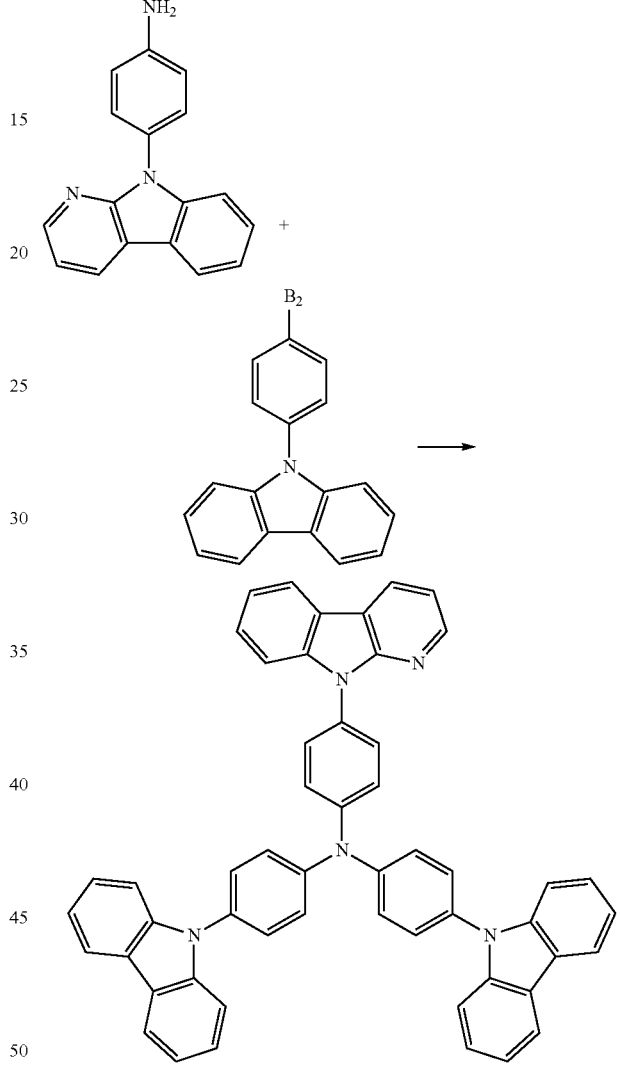

4-(N-carbolinyl)benzenamine 2 g (7.7 mmol), N-(4-bromophenyl)-α-carbazole 5.5 g (18 mmol), toluene 50 ml, sodium-tert-butoxide 2.2 g (23 mmol), Pd2(dba)3 0.3 g (0.3 mmol) and tris-tert-butylphosphine 0.4 g (2 mmol) are put in a 100 ml two-neck flask and refluxed under a condition of nitrogen and for 12 hours. After completion of the reaction, the resulted mixture is cooled to a room temperature and precipitated by adding methanol 100 ml. Then, the mixture is resolved in methylenchloride and absorbed by silicagel. The mixture is filtered by silicagel column chromatography with THF such that white powder 3.6 g is obtained. (yield: 63%)

Figure 6:
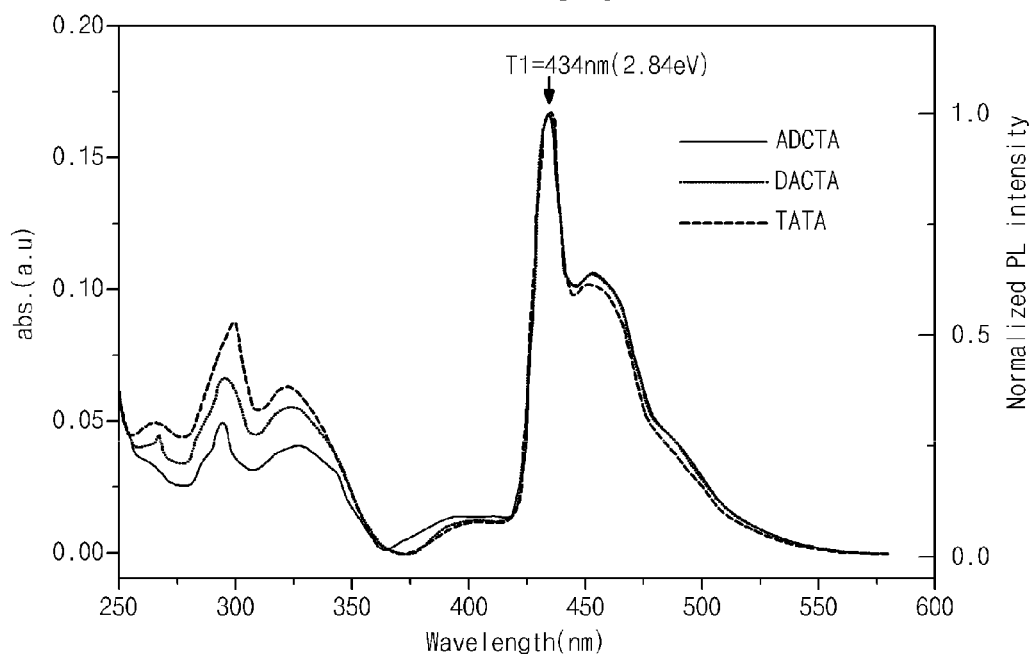
FIG. 6 shows UV spectrums and PL spectrums of phosphorescent compounds according to the fourth to sixth embodiments of the present invention.

FIG. 6 shows UV spectrums and PL spectrums of phosphorescent compounds in the fourth to sixth embodiments of the present invention. FIG. 6 shows the spectrums of

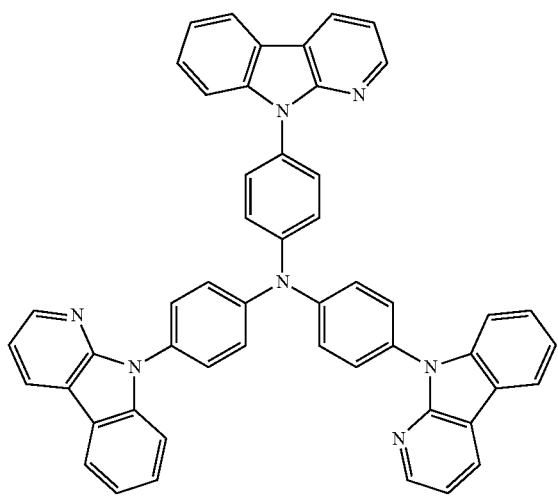 [SMILES: c1ccc2c(c1)c1cccnc1n2-c1ccc(N(c2ccc(-n3c4ccccc4c4cccnc43)cc2)c2ccc(-n3c4ccccc4c4cccnc43)cc2)cc1]

in the above Formula 8 ("TATA" line),

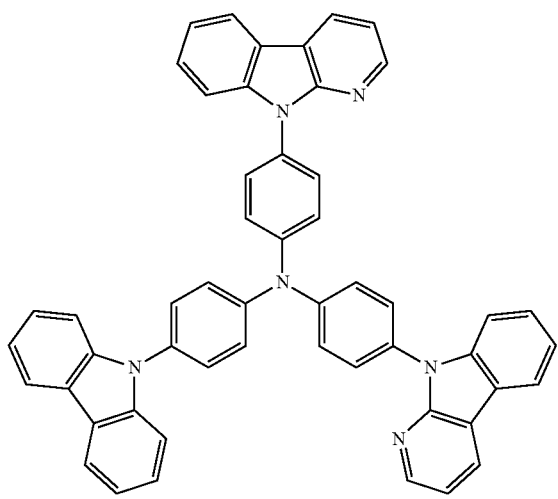 [SMILES: c1ccc2c(c1)c1ccccc1n2-c1ccc(N(c2ccc(-n3c4ccccc4c4cccnc43)cc2)c2ccc(-n3c4ccccc4c4cccnc43)cc2)cc1]

in the above Formula 10 ("DACTA" line), and

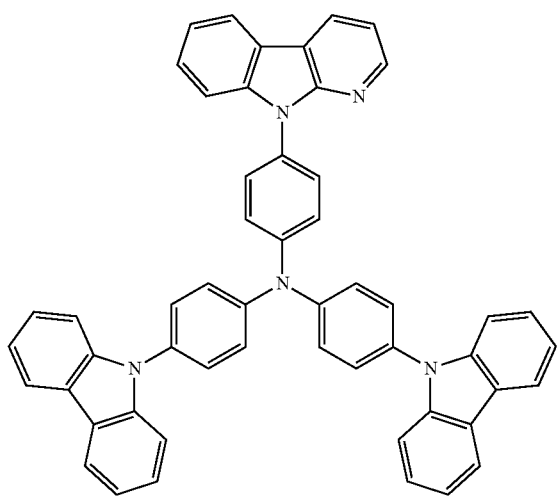 [SMILES: c1ccc2c(c1)c1ccccc1n2-c1ccc(N(c2ccc(-n3c4ccccc4c4ccccc43)cc2)c2ccc(-n3c4ccccc4c4cccnc43)cc2)cc1]

in the above Formula 12 ("ADCTA" line).

As shown in FIG. 6, the phosphorescent compounds according to the fourth to sixth embodiments of the present invention have a triplet energy above 2.8 eV. A triplet energy of the phosphorescent compounds in the present invention is larger than that of the related art compound, i.e., CBP, and that of the related art phosphorescent dopant. Accordingly, an energy counter-transition from the dopant to the host is prevented such that an emission yield is improved.

In addition, since the phosphorescent compound in the fourth to sixth embodiments of the present invention has the triplet energy larger than the dopant, the phosphorescent compound can be used for the hole transporting layer or the electron transporting layer. An energy counter-transition from the dopant to the hole transporting layer or the electron transporting layer is also prevented.

Referring to FIG. 4, which is a schematic cross-sectional view of an OELD according to the present invention, the OELD includes a first substrate (not shown), a second substrate (not shown) and an organic electroluminescent diode E between the first and second substrates.

The organic electroluminescent diode E includes a first electrode 110, a second electrode 130 and an organic emitting layer 120. The first electrode 110 is formed of a material having a relatively high work function to serve as an anode. For example, the first electrode 110 may be formed of indium-tin-oxide (ITO). The second electrode 130 is formed of a material having a relatively low work function to serve as a cathode. For example, the second electrode 130 may be formed of aluminum (Al) or Al alloy.

The organic emitting layer 120 includes red, green and blue organic emitting pattern. To increase an emission efficiency, the organic emitting layer 120 includes a hole injection layer (HTL) 121, a hole transporting layer (HIL) 122, an emitting material layer (EML) 123, an electron transporting layer (ETL) 124 and an electron injection layer (EIL) 125.

At least one of the emitting material layer 123, the hole transporting layer 122 and the electron transporting layer 124 includes the phosphorescent compound in one of the above Formulas 7, 9 and 11.

For example, when the emitting material layer 123 includes the phosphorescent compound in one of the above Formulas 7, 9 and 11 as a host, a dopant is doped with a weight % of about 1 to 10. Since the phosphorescent compound as the host has the triplet energy larger than the dopant, an energy counter-transition from the dopant to the host is prevented. As a result, an emission efficiency is improved. For example, the dopant may be iridium-bis(4,6-difluorophenylpyridineato-N,C2)-picolinate (FIrpic).

On the other hand, when the hole transporting layer 122 and/or the electron transporting layer 124 includes the phosphorescent compound in one of the above Formulas 7, 9 and 11, an energy counter-transition from the dopant to the hole transporting layer 122 and/or the electron transporting layer 124 is prevented because a triplet energy of the phosphorescent compound is larger than that of the dopant. Accordingly, the OELD has an improved energy efficiency.

—Seventh Embodiment—

A phosphorescent compound according to the seventh embodiment of the present invention includes one carboline group and one carbazole group at para-positions or meta-positions of benzene ring. The phosphorescent compound is represented by following Formulas 13 and 14.

[Formula 13]

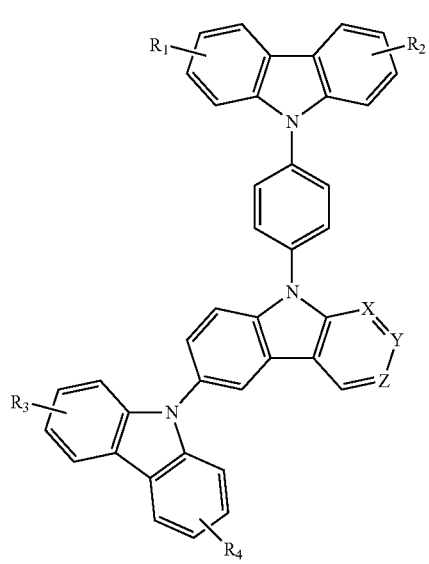

[Formula 14]

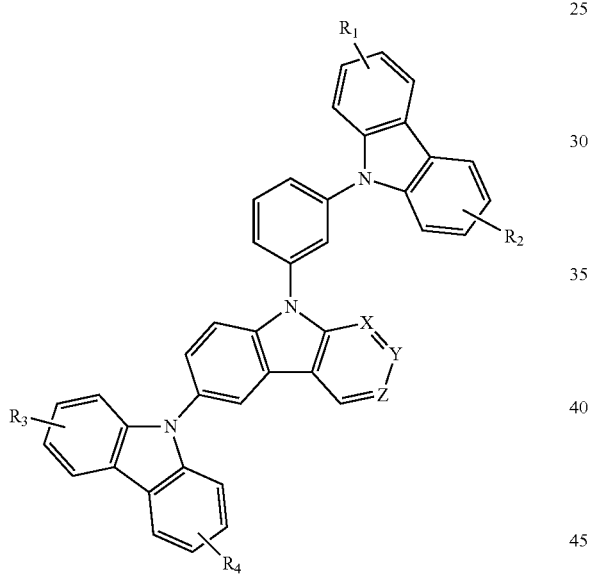

[Formula 15]

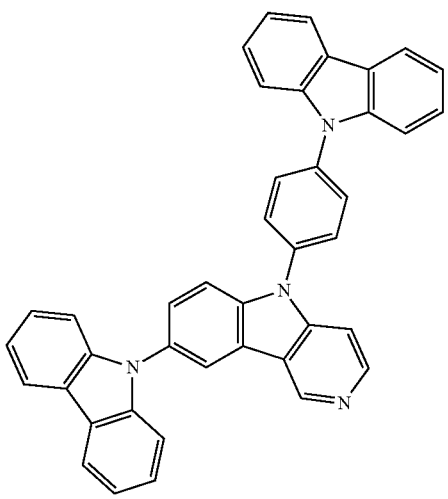

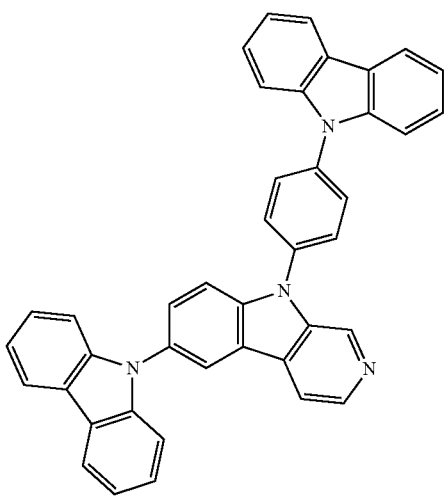

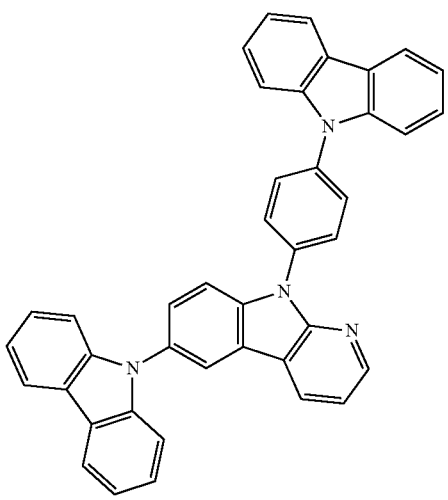

In the above Formulas 13 and 14, each of X, Y, Z is one of carbon and nitrogen, and at least one of X, Y, Z is nitrogen. For example, when X is nitrogen and both of Y and Z are carbon, carboline is referred to as α-carboline. When Y is nitrogen and both of X and Z are carbon, carboline is referred to as β-carboline. When Z is nitrogen and both of X and Y are carbon, carboline is referred to as γ-carboline.

In addition, in the above Formulas 13 and 14, each of R1, R2, R3 and R4 is one of hydrogen (H), fluorine (F), chlorine (Cl), aliphatic group, aromatic group, alkyl silyl group, aryl silyl group, alkoxy group, aryloxy group, alkyl phosphoryl group, alkyl sulfuryl group, aryl sulfuryl group, alkyl amino group and aryl amino group. For example, the aliphatic group may include C1 to C20 alkyl, and the aromatic group may include C6 to C20 aryl, such as phenyl, naphthyl, biphenyl, terphenyl and phenanthrenyl.

The phosphorescent compound in Formulas 13 and 14 is one of compounds in following Formula 15.

45
-continued

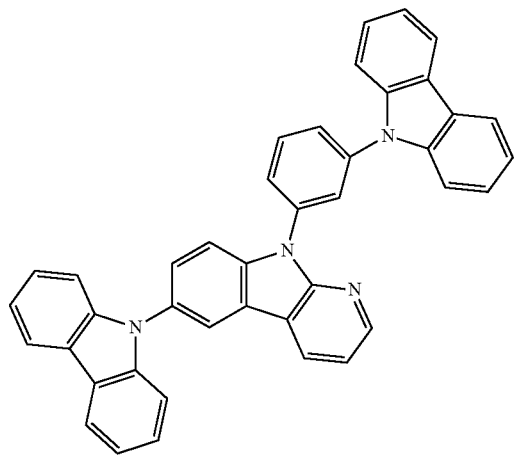

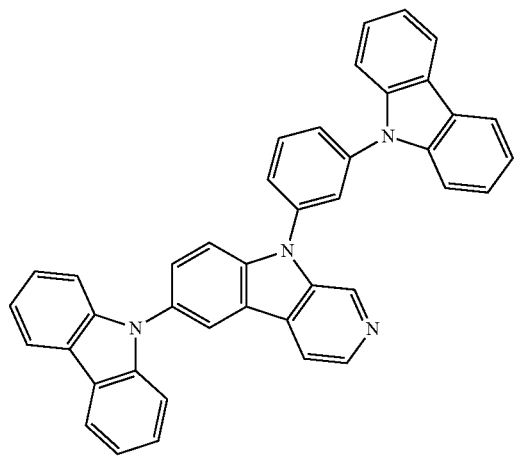

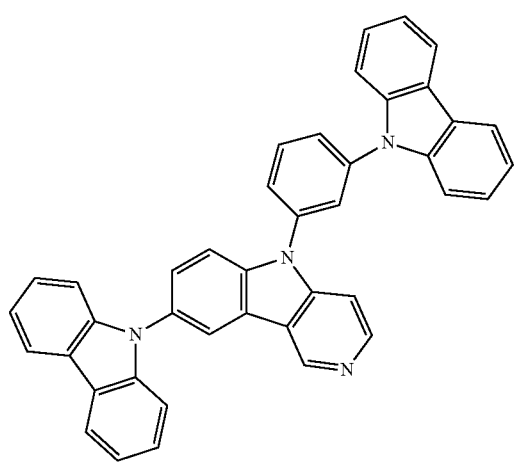

46

The phosphorescent compound represented by

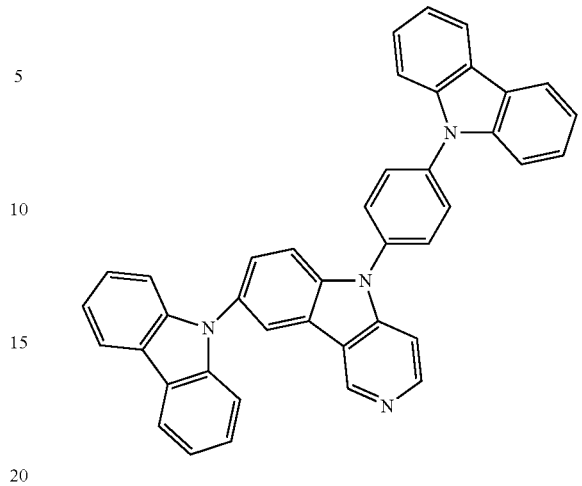

in the above Formula 15 is synthesized by following synthesis.

1. Synthesis of N-(4-iodophenyl)-carbazole
N-(4-iodophenyl)-carbazole is synthesized by following Reaction Formula 18.

[Reaction Formula 18]

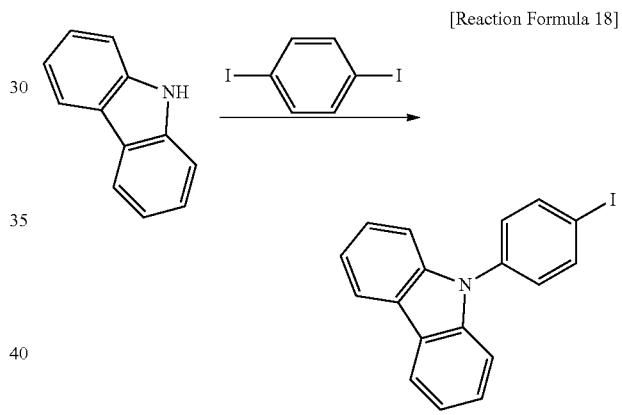

Carbazole 10 g (59.4 mmol), 1,4-di-iodobenzene 21.5 g (65.34 mmol), K3PO4 18.9 g, CuI 1.13 g, 1,2-diaminocyclohexane 1.45 g and 1,4-dioxane 100 ml are put in a 250 ml two-neck flask and refluxed for 12 hours. Water 100 ml is added to precipitate. The residence is filtered by a column chromatography with methylene chloride and hexane of 1:3 such that solid 7.0 g is obtained. (yield: 30%)

2. Synthesis of N-(4-N-carbazole)phenyl-3-bromopyridin-4-amine

N-(4-N-carbazole)phenyl-3-bromopyridin-4-amine is synthesized by following Reaction Formula 19.

[Reaction Formula 19]

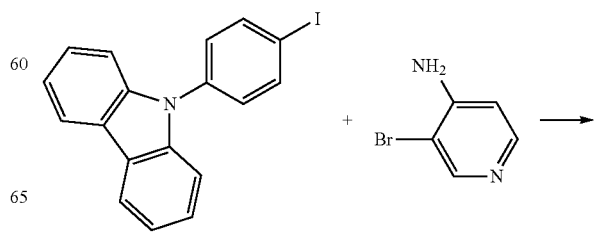

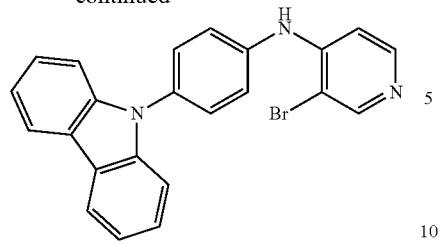

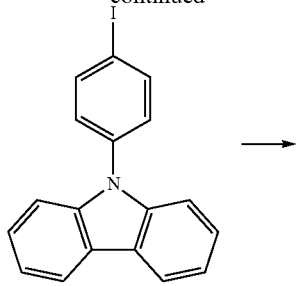

N-(4-iodophenyl)-carbazole 10 g (27.1 mmol), 3-bromopyridin-4-amine 4.68 g (27.1 mmol), sodium-tert-butoxide 5.2 g, Pd$_2$(dba)$_3$ 0.49 g, xanthophos 0.62 g and toluene 80 ml are put in a 100 ml two-neck flask and refluxed for 24 hours. After completion of the reaction, toluene is removed by distillation under reduced pressure and water 100 ml is added. The resulting solution is extracted using ethyl acetate and filtered by colum chromatrography such that solid 10 g is obtained. (yield: 88%)

3. Synthesis of 8-(N-carbazolyl)-γ-carboline 8-(N-carbazolyl)-γ-carboline is synthesized by following Reaction Formula 20.

[Reaction Formula 20]

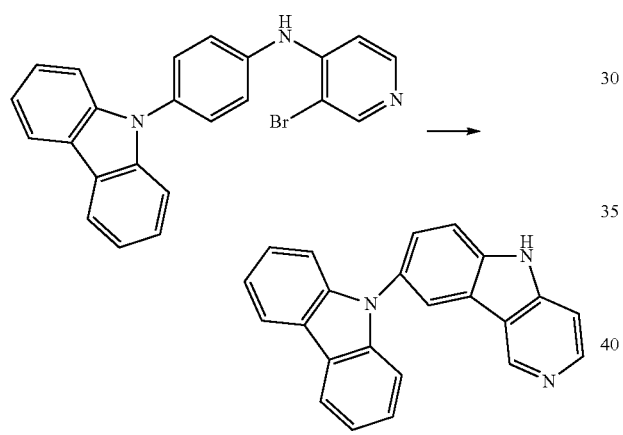

N-(4-N-carbazolyl)phenyl-3-bromopyridin-4-amine 10 g (24 mmol), pd(acetate)2 0.18 g, 2-(dicyclohexylphosphino)biphenyl 0.5 g, undecene 6 ml and dimethyl acetamide 50 ml are put in a 100 ml two-neck flask and refluxed for 24 hours. After completion of the reaction, the reaction mixture is cooled and water 50 ml is added such that sediment 4.1 g is obtained. (yield: 49%)

4. Synthesis of N-(4-(N-carbazole)phenyl)-8-(N-carbazole)-γ-carboline

N-(4-(N-carbazole)phenyl)-8-(N-carbazole)-γ-carboline carboline is synthesized by following Reaction Formula 21.

[Reaction Formula 21]

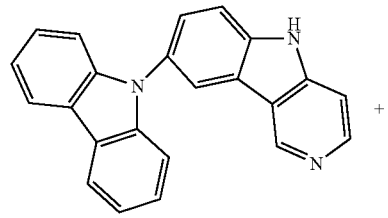

+

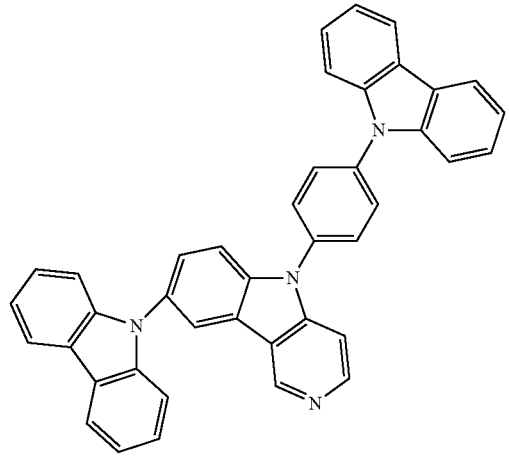 [SMILES: c1ccc2c(c1)c1ccccc1n2-c1ccc(-n2c3ccncc3c3cc(-n4c5ccccc5c5ccccc54)ccc32)cc1]

8-(N-carbazolyl)-γ-carboline 4.0 g (11.9 mmol), N-(4-iodophenyl)-carbazole 5.0 g (13.5 mmol), dioxane 50 ml, CuI 0.2 g, trans-diaminocyclohexane 0.3 g and K$_3$PO$_4$ 4 g are put in a 100 ml two-neck flask and refluxed for 12 hours. After completion of the reaction, the resulting solution is filtered to remove salt. Water 50 ml is added into the solution to precipitate. The residence is filtered by colum chromatrography with ethylene acetate and hexane of 1:1 such that white powder 2.5 g is obtained. (yield: 50%)

Figure 7:
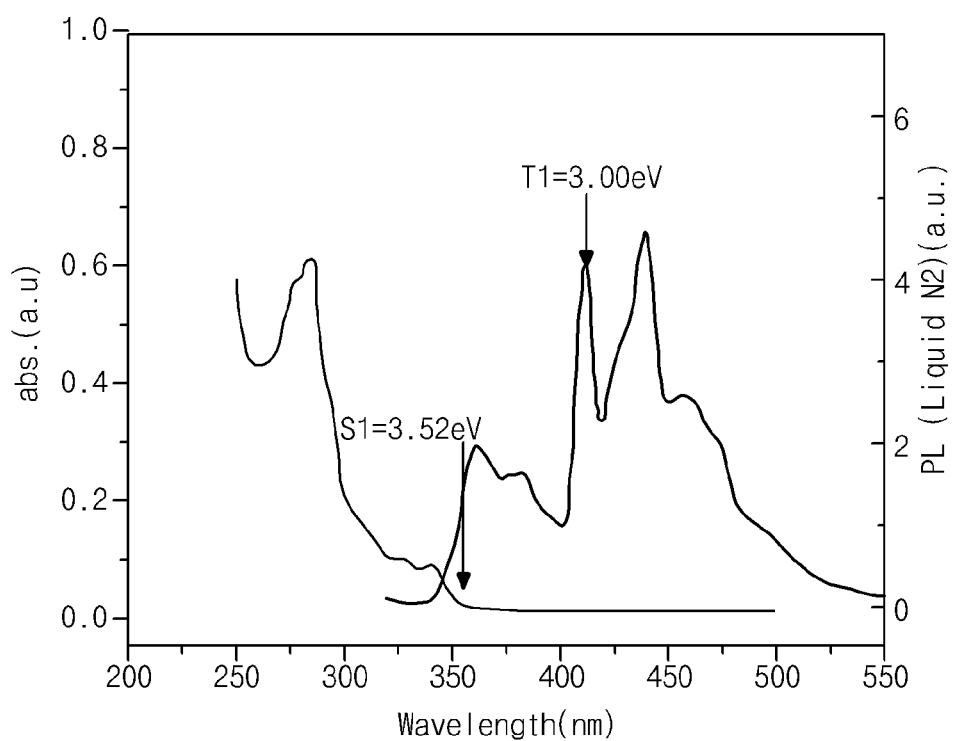
FIG. 7 shows a UV spectrum and a PL spectrum of a phosphorescent compound according to the seventh embodiment of the present invention.

FIG. 7 shows a UV spectrum and a PL spectrum of a phosphorescent compound according to the seventh embodiment of the present invention. FIG. 6 shows the spectrums of

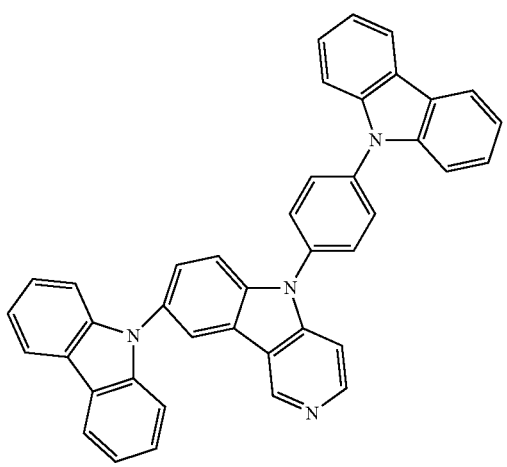 [SMILES: c1ccc2c(c1)c1ccccc1n2-c1ccc(-n2c3ccncc3c3cc(-n4c5ccccc5c5ccccc54)ccc32)cc1]

in the above Formula 15.

As shown in FIG. 7, the phosphorescent compounds according to the seventh embodiment of the present invention have a triplet energy above 2.8 eV. A triplet energy of the phosphorescent compounds in the present invention is larger than that of the related art compound, i.e., CBP, and that of the related art phosphorescent dopant. Accordingly, an energy counter-transition from the dopant to the host is prevented such that an emission yield is improved.

In addition, since the phosphorescent compound in the seventh embodiment of the present invention has the triplet energy larger than the dopant, the phosphorescent compound can be used for the hole transporting layer or the electron transporting layer. An energy counter-transition from the dopant to the hole transporting layer or the electron transporting layer is also prevented.

Referring to FIG. 4, which is a schematic cross-sectional view of an OELD according to the present invention, the OELD includes a first substrate (not shown), a second substrate (not shown) and an organic electroluminescent diode E between the first and second substrates.

The organic electroluminescent diode E includes a first electrode 110, a second electrode 130 and an organic emitting layer 120. The first electrode 110 is formed of a material having a relatively high work function to serve as an anode. For example, the first electrode 110 may be formed of indium-tin-oxide (ITO). The second electrode 130 is formed of a material having a relatively low work function to serve as a cathode. For example, the second electrode 130 may be formed of aluminum (Al) or Al alloy.

The organic emitting layer 120 includes red, green and blue organic emitting pattern. To increase an emission efficiency, the organic emitting layer 120 includes a hole injection layer (HTL) 121, a hole transporting layer (HIL) 122, an emitting material layer (EML) 123, an electron transporting layer (ETL) 124 and an electron injection layer (EIL) 125.

At least one of the emitting material layer 123, the hole transporting layer 122 and the electron transporting layer 124 includes the phosphorescent compound in one of the above Formulas 13 and 14.

For example, when the emitting material layer 123 includes the phosphorescent compound in one of the above Formulas 13 and 14 as a host, a dopant is doped with a weight % of about 1 to 10. Since the phosphorescent compound as the host has the triplet energy larger than the dopant, an energy counter-transition from the dopant to the host is prevented. As a result, an emission efficiency is improved. For example, the dopant may be iridium-bis(4,6-difluorophenylpyridineato-N,C2)-picolinate (FIrpic).

On the other hand, when the hole transporting layer 122 and/or the electron transporting layer 124 includes the phosphorescent compound in one of the above Formulas 13 and 14, an energy counter-transition from the dopant to the hole transporting layer 122 and/or the electron transporting layer 124 is prevented because a triplet energy of the phosphorescent compound is larger than that of the dopant. Accordingly, the OELD has an improved energy efficiency.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A phosphorescent compound, represented by the following Formula:

[Formula]

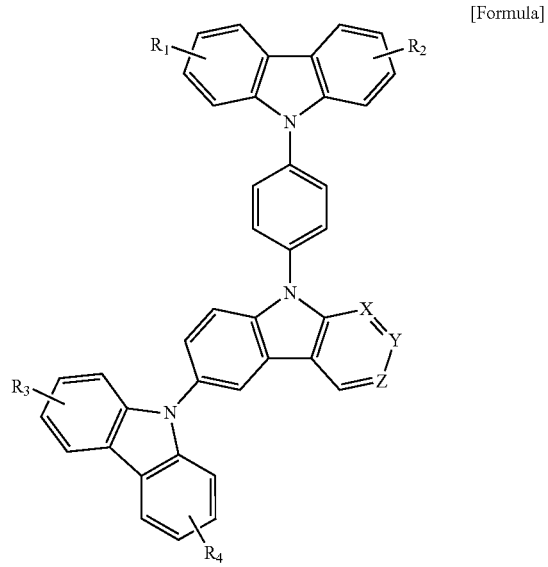

wherein:
each of X, Y and Z is one of carbon and nitrogen, where at least one of X, Y and Z is nitrogen; and
each of $R_1$, $R_2$, $R_3$ and $R_4$ is one of hydrogen (H), fluorine (F), chlorine (Cl), an aliphatic group, an aromatic group, an alkyl silyl group, an aryl silyl group, an alkoxy group, an aryloxy group, an alkyl phosphoryl group, an alkyl sulfuryl group, an aryl sulfuryl group, an alkyl amino group and an aryl amino group.

2. The compound according to claim 1, wherein the aliphatic group is selected from C1 to C20 alkyl, and the aromatic group is selected from C6 to C20 aryl.

3. The compound according to claim 2, wherein the aryl group is selected from the group consisting of phenyl, naphthyl, biphenyl, terphenyl and phenanthrenyl.

4. A phosphorescent compound, represented by the following Formula:

[Formula]

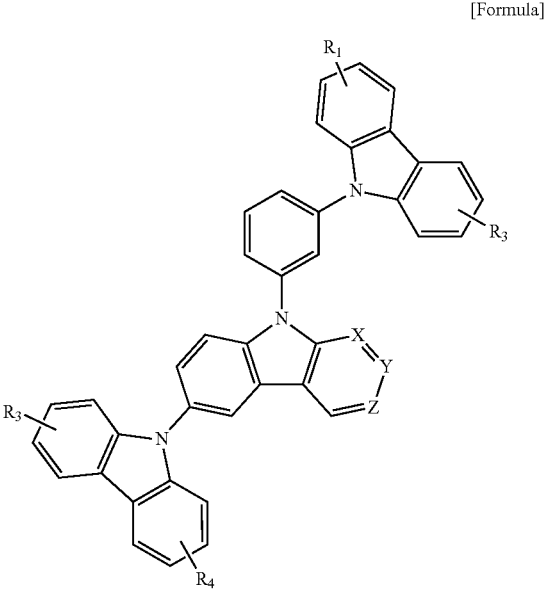

wherein:
each of X, Y and Z is one of carbon and nitrogen, where at least one of X, Y and Z is nitrogen; and
each of $R_1$, $R_2$, $R_3$ and $R_4$ is one of hydrogen (H), fluorine (F), chlorine (Cl), an aliphatic group, an aromatic group, an alkyl silyl group, an aryl silyl group, an alkoxy group, an aryloxy group, an alkyl phosphoryl group, an alkyl sulfuryl group, an aryl sulfuryl group, an alkyl amino group and an aryl amino group.

5. The compound according to claim 4, wherein the aliphatic group is selected from C1 to C20 alkyl, and the aromatic group is selected from C6 to C20 aryl.

6. The compound according to claim 5, wherein the aryl group is selected from the group consisting of phenyl, naphthyl, biphenyl, terphenyl and phenanthrenyl.

7. An organic electroluminescent device, comprising:
a first electrode;
a second electrode facing the first electrode; and
an emitting material layer between the first and second electrodes,
wherein the emitting material layer comprises a host represented by the following Formula and a dopant,

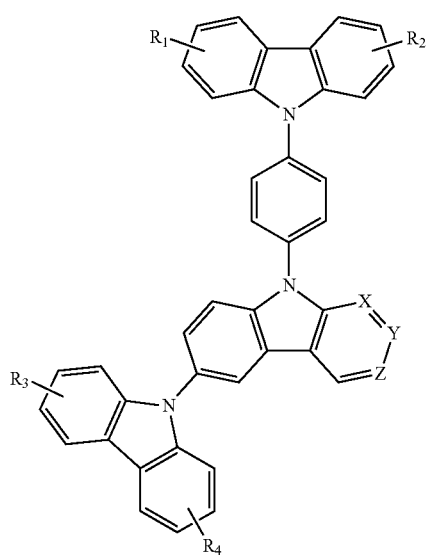

[Formula]

wherein:
each of X, Y and Z is one of carbon and nitrogen, where at least one of X, Y and Z is nitrogen; and
each of $R_1$, $R_2$, $R_3$ and $R_4$ is one of hydrogen (H), fluorine (F), chlorine (Cl), an aliphatic group, an aromatic group, an alkyl silyl group, an aryl silyl group, an alkoxy group, an aryloxy group, an alkyl phosphoryl group, an alkyl sulfuryl group, an aryl sulfuryl group, an alkyl amino group and an aryl amino group.

8. The device according to claim 7, further comprising:
a hole injection layer between the first electrode and the emitting material layer;
a hole transporting layer between the hole injection layer and the emitting material layer;
an electron injection layer between the second electrode and the emitting material layer; and
an electron transporting layer between the electron injection layer and the emitting material layer,
wherein at least one of the hole transporting layer and the electron transporting layer comprises a host represented by the Formula.

9. An organic electroluminescent device, comprising:
a first electrode;
a second electrode facing the first electrode; and
an emitting material layer between the first and second electrodes,
wherein the emitting material layer comprises a host represented by the following Formula and a dopant,

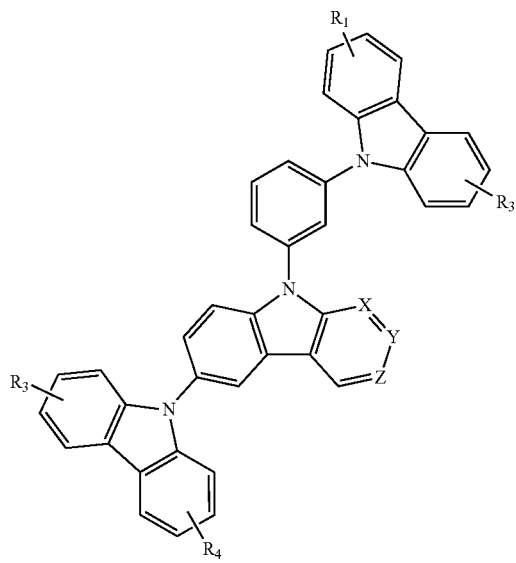

[Formula]

wherein:
each of X, Y and Z is one of carbon and nitrogen, where at least one of X, Y and Z is nitrogen; and
each of $R_1$, $R_2$, $R_3$ and $R_4$ is one of hydrogen (H), fluorine (F), chlorine (Cl), an aliphatic group, an aromatic group, an alkyl silyl group, an aryl silyl group, an alkoxy group, an aryloxy group, an alkyl phosphoryl group, an alkyl sulfuryl group, an aryl sulfuryl group, an alkyl amino group and an aryl amino group.

10. The device according to claim 9, further comprising:
a hole injection layer between the first electrode and the emitting material layer;
a hole transporting layer between the hole injection layer and the emitting material layer;
an electron injection layer between the second electrode and the emitting material layer; and
an electron transporting layer between the electron injection layer and the emitting material layer,
wherein at least one of the hole transporting layer and the electron transporting layer comprises a host represented by the Formula.

* * * * *